United States Patent [19]

Christensen et al.

[11] 4,311,704
[45] Jan. 19, 1982

[54] SUBSTITUTED N-METHYLENE DERIVATIVES OF THIENAMYCIN

[75] Inventors: Burton G. Christensen, Metuchen; William J. Leanza, Berkeley Heights; David H. Shih, Edison; Kenneth J. Wildonger, Somerville, all of N.J.

[73] Assignee: Merck & Co., Inc., Rahway, N.J.

[21] Appl. No.: 159,573

[22] Filed: Jun. 16, 1980

Related U.S. Application Data

[63] Continuation of Ser. No. 803,177, Jun. 3, 1977, abandoned.

[51] Int. Cl.³ .............. C07D 487/04; A61K 31/40; A61K 31/44; A61K 31/425
[52] U.S. Cl. .............. 424/274; 260/245.2 T; 424/270; 424/263; 546/272; 548/181
[58] Field of Search .............. 260/245.2 T; 424/274, 424/265, 270; 546/272; 548/181

[56] References Cited

U.S. PATENT DOCUMENTS 4,172,144 10/1979 Bouffard et al. ............ 260/245.2 T
4,194,047 3/1980 Christensen et al. ........ 260/245.2 T
4,232,030 11/1980 Christensen ................. 260/245.2 T

*Primary Examiner*—Mark L. Berch
*Attorney, Agent, or Firm*—Frank M. Mahon; James A. Arno; Hesna J. Pfeiffer

[57] ABSTRACT

Disclosed are substituted N-methylene derivatives of thienamycin having the formula:

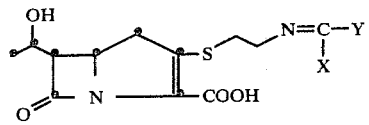

wherein:
(1.) X=—NR¹R², and Y=—R'—N=CRNR¹R², and (2.) X=R, and Y=—NR¹R'N=CRNR¹R²; and wherein: R is, inter alia, hydrogen, $NH_2$, —$NHR^1$, —$NR^1R^2$, $R^1$ and $R^2$; $R^1$ and $R^2$ are independently selected from: hydrogen, substituted, or unsubstituted: alkyl, alkenyl, alkynyl, cycloalkyl, cycloalkylalkyl, aryl, aralkyl, heteroaryl, heteroaralkyl, heterocyclyl, and heterocyclylalkyl; R' is —$(CH_2)_n$—, n is 1-6, or —$(CH_2)_m$—Q—$(CH_2)_p$—, m, n=1-3 and Q is O, S or R' is a carbocyclic or heterocyclic ring. Such compounds and their pharmaceutically acceptable salt, ether, ester and amide derivatives are useful as antibiotics. Also disclosed are processes for the preparation of such compounds, pharmaceutical compositions comprising such compounds; and methods of treatment comprising administering such compounds and compositions when an antibiotic effect is indicated.

15 Claims, No Drawings

SUBSTITUTED N-METHYLENE DERIVATIVES OF THIENAMYCIN

This is a continuation of application Ser. No. 803,177, filed June 3, 1977, now abandoned.

BACKGROUND OF THE INVENTION

This invention relates to certain substituted N-methylene derivatives of the new antibiotic thienamycin. Such compounds and their pharmaceutically acceptable salt, ether, ester, and amide derivatives are useful as antibiotics. This invention also relates to processes for the preparation of such compounds; pharmaceutical compositions comprising such compounds; and methods of treatment comprising administering such compounds and compositions when an antibiotic effect is indicated.

Thienamycin is disclosed and claimed in U.S. Pat. No. 3,950,357 issued Apr. 13, 1976. This patent is incorporated herein by reference since thienamycin may be employed as a starting material in the preparation of the compounds of the present invention. Thienamycin is known to have the following structure:

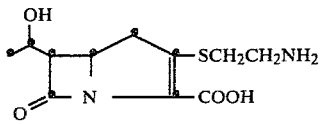

Starting material I (including all isomers and mixtures of such isomers) is also available by the total synthesis which is described and claimed in co-pending, commonly assigned U.S. patent application Ser. No. 792,071 filed Apr. 28, 1977 now abandoned in favor of U.S. patent application Ser. No. 833,210, filed Sept. 15, 1977, now abandoned in favor of U.S. patent application Ser. No. 17,680, filed Mar. 5, 1979, now U.S. Pat. No. 4,234,596, issued Nov. 18, 1980. This application is incorporated herein by reference since it makes available all isomers, pure and as mixtures, of I which are suitable starting materials for the preparation of the compounds of the present invention.

The compounds of the present invention may be represented by the following structural formulae (II):

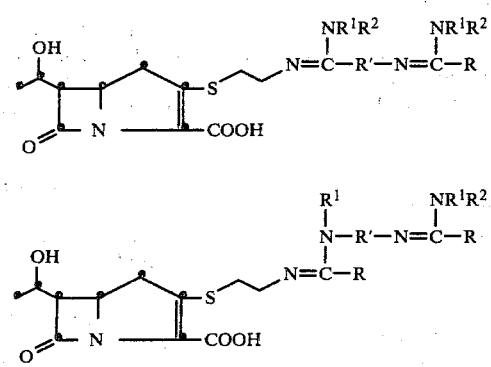

which structures represent, respectively, one canonical form of a single resonant structure:

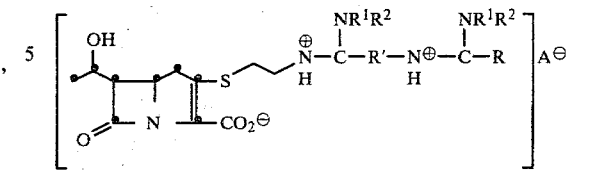

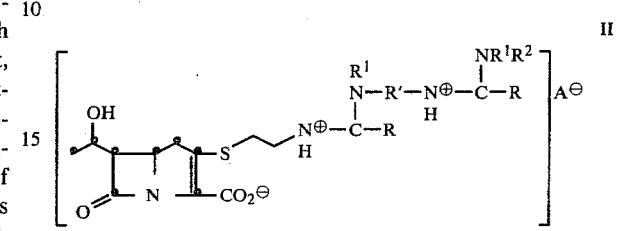

wherein: R, $R^1$, $R^2$, R' and the counter anion A are defined below.

For convenience, the compounds of the present invention may be represented by the following symbolism:

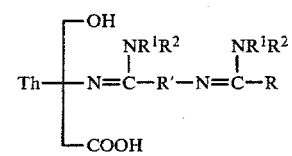

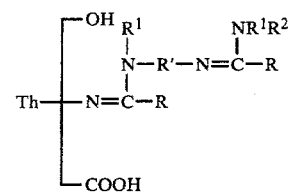

or collectively,

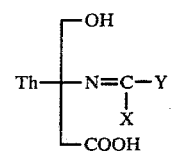

wherein: (1.) $X=-NR^1R^2$, and $Y=-R'-N=CNR^1R^2$; and (2.) $X=R$, and $Y=-NR^1R'N=CNR^1R^2$; "Th" indicates the bicyclic nucleus of thienamycin wherein its hydroxyl, amino and carboxyl functional groups are shown: R is independently selected from the group consisting of hydrogen, $-NH_2$, $-NHR^1$, $-NR^1R^2$, $R^1$ and $R^2$; $R^1$ and $R^2$ are independently selected from hydrogen, alkoxyl, having 1-6 carbon atoms, $R^1$ and $R^2$ may be joined together to form a substituted or unsubstituted mono- or bicyclic heteroaryl or heterocyclyl comprising (together with the nitrogen atom to which they are attached) 4–16 atoms one or more of which may be an additional hetero atom selected from oxygen, sulphur or nitrogen; R, $R^1$ and $R^2$ are substituted or unsubstituted: alkyl having from 1 to about 10 carbon atoms; alkenyl having from 2 to about 10 carbon atoms; alkynyl having from 2 to about 10 carbon atoms; cycloalkyl having from 3 to 10 carbon atoms; cycloalkylalkyl and cycloalkylalkenyl having from 4 to 12 carbon atoms; cycloalkenyl, cycloalkenylalkenyl, and cycloalkenylalkyl having 3–10, 4–12 and 4–12 carbon atoms, respectively; aryl having from 6 to 10 carbon atoms, aralkyl, aralkenyl, and aralkynyl having from 7 to 16 carbon atoms; mono- and bicyclic heteroaryl and heteroaralkyl which typically comprise 6 to 16 ring atoms one or more of which is a hetero atom selected from oxygen, sulphur, or nitrogen and wherein the alkyl moiety of the heteroaralkyl radical comprises 1 to about 6 carbon atoms; mono- and bicyclic heterocyclyl and heterocyclylalkyl which typically comprises 4 to 16 ring atoms one or more of which is a hetero atom selected from oxygen, sulphur or nitrogen and wherein the alkyl moiety of the heterocyclylalkyl radical comprises from 1 to about 6 carbon atoms; and wherein the above-mentioned substituent or substituents on R, R¹, R² or on the ring formed by the joinder of R¹ and R², are selected from the group consisting of: halo, such as chloro, bromo, iodo and fluoro; azido; alkyl having 1–4 carbon atoms; thio; sulpho; phosphono; cyanothio (—SCN); nitro; amine; hydrazino; mono-, di- and trialkyl substituted amino, and hydrazino wherein the alkyl has 1–6 carbon atoms; hydroxyl; alkoxyl having 1–6 carbon atoms; alkylthio having 1–6 carbon atoms; carboxyl; oxo; alkoxylcarbonyl having 1–6 carbon atoms in the alkoxyl moiety, acyloxy comprising 2–10 carbon atoms; carbamoyl and mono- and dialkylcarbamoyl wherein the alkyl groups have 1–4 carbon atoms;

R' is substituted or unsubstituted:
—(CH₂)$_{\overline{n}}$ (n=1–6),
—(CH₂)$_{\overline{m}}$—Q—(CH₂)$_{\overline{p}}$(n, m=1–3), (Q=S or O), or

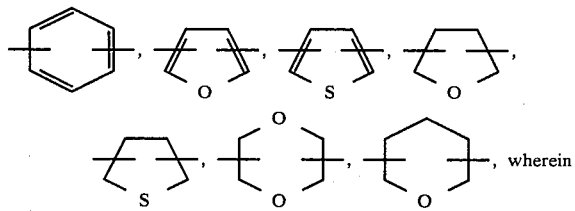

, wherein the substituent on R' is OH, —OR°, —SR° or R° (R°=alkyl having 1–4 carbon atoms); the non-critical counter, A, is representatively selected to provide pharmaceutically acceptable salts such as halides (chloro, bromo and the like), sulfate, phosphate, citrate, acetate, benzoate and the like; finally, representative heterocyclic values for R, R¹ and R² (defined above) are given in the following table.

| Heteroaryl | Heteroaralkyl | Heterocyclyl | Heterocyclylalkyl |
|---|---|---|---|
|  | 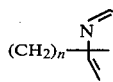 |  | 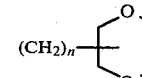 |
|  |  |  | 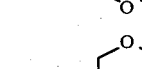 |
|  | 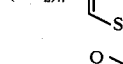 |  | 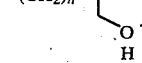 |
|  | 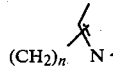 |  | 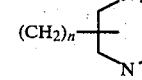 |
|  |  |  |  |

[n = 1–6]

The compounds of the present invention also embrace embodiments of the following structure:

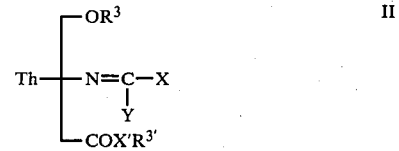    II wherein:
X' is oxygen, sulphur or NR'' (R'' is hydrogen or R³');
R³' is hydrogen, or, inter alia, is representatively selected to provide the pharmaceutically acceptable salt, ester, anhydride (R³' is acyl), and amide moieties known in the bicyclic β-lactam antibiotic art—such moieties are enumerated in greater detail below; and R³ is: 1.) acyl (generically the group OR³ is classifiable as an ester); or 2.) R³ is selected from alkyl, aryl, alkenyl, aralkyl and the like, such that the group OR³ is generically classifiable as an ether. R³ may also be hydrogen. The term "acyl" is by definition inclusive of the alkanoyls including derivatives and analogues thereof such as thio analogues wherein the carbonyl oxygen is replaced by sulphur; as well as sulphur and phosphorous acyl analogues such as substituted sulfonyl-, sulfinyl-, and sulfenyl radicals, and substituted P(III and V) radicals such as substituted phosphorous-, phosphoric-, phosphonous- and phosphonic radicals. Such radicals, R³, of the present invention are enumerated in greater detail below.

There is a continuing need for new antibiotics. For unfortunately, there is no static effectiveness of a given antibiotic because continued wide scale usage of any such antibiotic selectively gives rise to resistant strains of pathogens. In addition, the known antibiotics suffer from the disadvantage of being effective only against certain types of microorganisms. Accordingly, the search for new antibiotics continues.

Unexpectedly, it has been found that the compounds of the present invention are broad spectrum antibiotics, which are useful in animal and human therapy and in inanimate systems.

Thus, it is an object of the present invention to provide a novel class of antibiotics which possess the basic nuclear structure of thienamycin (I), but which are characterized as the substituted N-methylene derivatives thereof. These antibiotics are active against a broad range of pathogens which representatively include both gram positive bacteria such as *S. aureus, Strep. pyogenes,* and *B. subtilis* and gram negative bacteria such as *E. coli, Proteus morganii,* Klebsiella, Serratia, and Pseudomonas. Further objects of this invention are to provide chemical processes for the preparation of such antibiotics and their non-toxic pharmaceutically acceptable salt, ether, ester and amide derivatives; pharmaceutical compositions comprising such antibiotics; and to provide methods of treatment comprising administering such antibiotics and composition when an antibiotic effect is indicated.

DETAILED DESCRIPTION OF THE INVENTION

The compounds of the present invention are conveniently prepared by amidination of an amino-amidine or amino-guanidine derivative of thienamycin ($\underline{1}$):

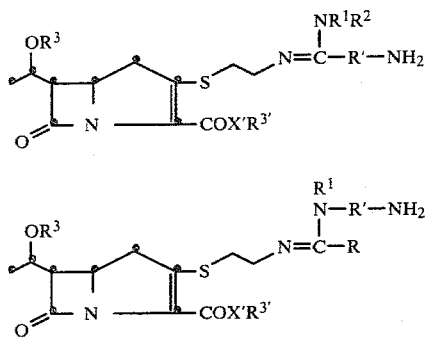

or, for convenience:

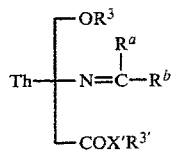

wherein all symbolism is as previously defined and $R^a = -NR^1R^2$ when $R^b = -R'-NH_2$; and $R^a = -NR^1R'NH_2$ when $R^b = R$. The values for $R^3$, $X'$ and $R^{3'}$ are further defined below.

The starting materials 1 are fully disclosed and claimed in co-pending, commonly assigned U.S. patent application Ser. No. 733,654 filed Oct. 18, 1976 now abandoned in favor of U.S. patent application Ser. No. 852,425, filed Nov. 17, 1977, now U.S. Pat. No. 4,194,047, issued Mar. 18, 1980 which application is incorporated herein by reference to the extent that it describes the preparation of $\underline{1}$.

In general the starting amidines ($\underline{1}$) are prepared according to the following scheme:

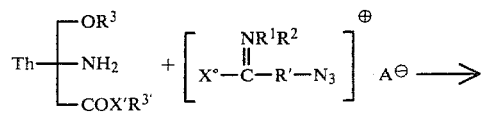

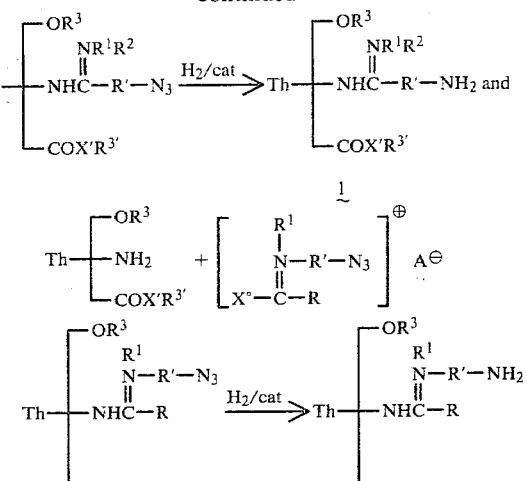

wherein all symbolism is as previously defined and $X°$ is a leaving group such as chloro, bromo or the leaving group $-OR°$ and $SR°$ wherein $R°$ is lower alkyl such as methyl, ethyl or the like; and A is a counter anion such as chloro, iodo, $BF_4^-$, $PF_6^-$, $SbF_6^-$ or the like.

In words relative to the above reaction schemes, the thienamycin starting material in a solvent such as water, dioxane, tetrahydrofuran(THF), dimethylsulfoxide(DMSO), hexamethylphosphoramide(HMPA), aqueous phosphate buffer (pH 8–9) mixtures (1:1) of solvents such as dioxane or THF or the like is treated with the indicated reagent at a temperature of from $-10°$ to $40°$ C. for from 0.5 to 4 hours to provide the intermediate azide which is reduced, preferably in a solvent such as water, ethanol and aqueous ethanol or the like under 1 to 40 atmospheres of $H_2$ in the presence of a metal catalyst such as 10% Pd/charcoal, PdO, PtO, Rh(Cl)(P$\phi_3$)CO ($\phi$=phenyl), Raney nickel or the like at a temperature of from $0°$ to $40°$ C., for from 0.1 to 6 hours.

The compounds of the present invention (II, above) are prepared from 1 on treatment with an imido ester (a) or an imido halide (b):

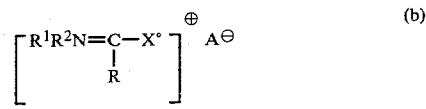

wherein $R^1$, $R^2$ and R are as defined above and $X''R°$ is a leaving group wherein $X''$ is O or S and $R°$ is loweralkyl such as methyl, ethyl or the like and $X°$ is halo such as chloro or bromo and A is a counter anion such as chloro, bromo, $BF_4^-$, $PF_6^-$, $SbF_6^-$ or the like. Reagents (a.) and (b.) are representatively enumerated below.

Suitable solvents for the preparation of the compounds of the present invention ($\underline{1}$+a. or b.→II) according to the above reaction schemes, and depending upon the identity of the thienamycin substrate and reagent include: water, dioxane, tetrahydrofuran (THF), dimethylformamide (DMF), chloroform, acetone, acetonitrile or mixtures thereof. The reaction is conducted at a temperature of from 0° to about 25° C. for from 1 to about 6 hours. There is no criticality as to the precise identity of the reaction solvent or the variables of reaction within the limits described above, provided only that the reaction solvent is inert or substantially inert to the intended course of reaction. Suitable reagents representatively include:

Imido Esters:

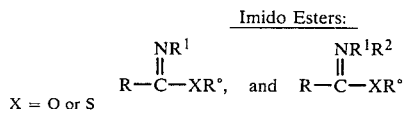

$X = O$ or $S$     (2.)

Methyl formimidate, ethyl formimidate, methyl acetimidate, ethyl acetimidate, methyl benzimidate, ethyl 4-pyridyl carboximidate, methyl phenylacetimidate, methyl 3-thienyl-carboximidate, methyl azidoacetimidate, methyl chloroacetimidate, methyl cyclohexylcarboximidate, methyl 2-furylcarboximidate, methyl p-nitrobenzimidate, methyl 2,4-dimethoxybenzimidate, ethyl N-methyl formimidate, methyl N-methyl formimidate, methyl N-isopropyl formimidate, and the like.

Such imido ester reagents (a.) are conveniently prepared by any of a variety of known procedures, such as:

(1.) The reaction of a nitrile, RCN, with a lower alkanol in the presence of HCl according to the well-known Pinner synthesis.

(2.) The reaction of a nitrile, RCN, with a lower alkanol in the presence of a base. Typically, the reaction is conducted at 0°–40° C. in the presence of an excess of the alcohol with a catalytic amount of an alkali metal alkoxide for from 15 minutes to 4 hours.

(3.) The reaction of an amide,

with an alkylchloroformate, such as methylchloroformate at 25° C.–45° C. for 1–4 hours.

(4.) The reaction of an N-substituted amide,

with an equivalent of an alkylating agent such as triethyloxonium fluoroborate in an inert solvent such as ether, chloroform, methylene chloride, or the like at 0°–23° C. for from 10 minutes to 12 hours.

(5.) The conversion of a readily available imido ester,

($R^1$ may be hydrogen), to a desired imido ester,

by reaction of the first-mentioned with an alkylamine, $R^1NH_2$, in a mixture of water and an immiscible solvent such as ether or chloroform at 0°–23° C. for from 5 minutes to 1 hour.

(b) Substituted Imido Halides:

Chloropiperidino methylium chloride, chlorodimethylforminium chloride, chlorodiethyl forminum chloride and the like.

Such imido halide reagents (b) are conveniently prepared by any of a variety of known procedures, such as:

(1.) The reaction of an N, N-disubstituted amide,

with a halogenating agent such as thionyl chloride, phosgene, phosphorous pentachloride or the like in an inert solvent such as chloroform, methylene chloride and the like at 0°–40° C. for from 1–5 hours.

The compounds of the present invention, II, may also be obtained by reacting 1 with an —OR° (e.g., O-alkyl, O-aryl) pseudorea or an S-alkyl or S-aryl pseudothiourea:

     (c.)

wherein $R^1$ and $R^2$ are as defined above and $X=O$ or $S$ and R° is as defined above and preferably is lower alkyl or aryl. Representative —OR° pseudourea and —SR° pseudothiourea reagents c. thus include: O-methyl pseudourea, S-Methylpseudothiourea, S-methylpseudothionitrourea, 0-2,4-dichlorophenyl pseudourea, S-p-nitrophenyl pseudothiourea, O-N,N-trimethylpseudourea, and the like.

Suitable solvents for such reactions (1+c.→II) include water and buffered aqueous polar organic solvent mixtures at pH 7–9 or anhydrous polar organic solvents such as dimethylformamide, dimethylsulfoxide or hexamethylphosphoramide at a temperature of from 0° C. to 40° C. for from 1 to 24 hours.

The following diagram summarizes the preparation of the compounds of the present invention, II, from starting materials 1 in reaction with reagents, a., b., and c.

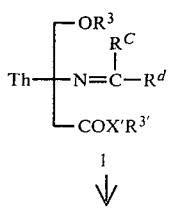

-continued

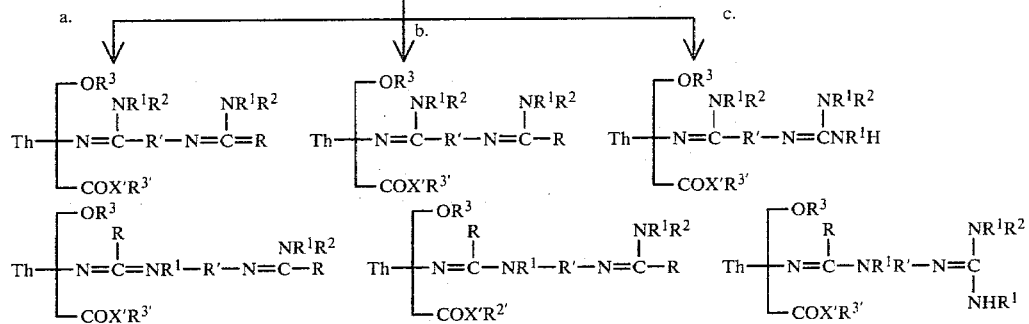

wherein all symbolism is as previously defined.

The products of this invention (II) form a wide variety of pharmacologically acceptable salts such as acid addition salts, e.g., with hydrochloric, hydrobromic, sulfuric, nitric, toluene-p-sulphonic and methane sulphonic acids. The salts of this invention are pharmacologically acceptable non-toxic derivatives which can be used as the active ingredient in suitable unit-dosage pharmaceutical forms. Also, they may be combined with other drugs to provide compositions having a broad spectrum of activity.

The novel compounds are valuable antibiotics active against various gram-positive and gram-negative bacteria and, accordingly, find utility in human and veterinary medicine. The compounds of this invention can therefore be used as antibacterial drugs for treating infections caused by gram-positive or gram-negative bacteria, for example, against *Staphylococcus aureus, Escherichia coli, Klebsiella pneumoniae, Serratia, Salmonella typhosa,* Pseudomonas and *Bacterium proteus. The antibacterials of the invention may further be utilized as additives to animal feeding stuffs, for preserving foodstuffs and as disinfectants. Forexample, they may be employed in aqueous compositions in concentrations ranging from 0.1 to 100 parts of antibiotic per million parts of solution in* order to destroy and inhibit the growth of harmful bacteria on medical and dental equipment and as bactericides in industrial applications, for example, in water-based paints and in the white water of paper mills to inhibit the growth of harmful bacteria.

The products of this invention may be used alone or in combination as an active ingredient in any one of a variety of pharmaceutical preparations. These antibiotics and their corresponding salts may be employed in capsule form or as tablets, powders or liquid solutions or as suspensions or elixirs. They may be adminstered orally, intravenously or intramuscularly.

The compositions are preferably presented in a form suitable for absorption by the gastro-intestinal tract. Tablets and capsules for oral administration may be in unit dose presentation form, and may contain conventional excipients such as binding agents, for example, syrup, acacia, gelatin, sorbitol, tragacanth, or polyvinylpyrrolidone; fillers for example, lactose, sugar, maize-starch, calcium phosphate, sorbitol or glycine; lubricants, for example, magnesium stearate, talc, polyethylene glycol, silic; disintegrants, for example, potato starch or acceptable wetting agents such as sodium lauryl sulphate. The tablets may be coated according to methods well known in the art. Oral liquid preparations may be in the form of aqueous or oily suspension, solution, emulsions, syrups, elixirs, etc. or may be presented as a dry product, for reconstitution with water or other suitable vehicles before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminum stearate gel or hydrogenated edible oils, for example almond oil, fractionated coconut oil, oily esters, propylene glycol, or ethyl alcohol; preservatives, for example methyl or propyl p-hydroxybenzoates or sorbic acid. Suppositories will contain conventional suppository bases, e.g. cocoa butter or other glyceride.

Compositions for injection may be presented in unit dose form in ampules, or in multidose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form for reconstitution with a suitable vehicle, e.g. sterile, pyrogen-free water, before use.

The compositions may also be prepared in suitable forms for absorption through the mucous membranes of the nose and throat or bronchial tissues and may conveniently take the form of powder or liquid sprays or inhalants, lozenges, throat paints, etc. For medication of the eyes or ears, the preparations may be presented as individual capsules, in liquid or semi-solid form, or may be used as drops etc. Topical applications may be formulated in hydrophobic or hydrophilic bases as ointments, creams, lotions, paints, powders, etc.

Also, in addition to a carrier, the instant compositions may include other ingredients such as stabilizers, binders, antioxidants, preservatives, lubricators, suspending agents, viscosity agents or flavoring agents and the like. In addition, there may also be included in the composition other active ingredients to provide a broader spectrum of antibiotic activity.

For veterinary medicine the composition may, for example, be formulated as an intramammary preparation in either long or quick-release bases.

The dosage to be administered depends to a large extent upon the condition of the subject being treated and the weight of the host, the route and frequency of administration, the parenteral route being preferred for generalized infections and the oral route for intestinal infections. In general, a daily oral dosage consists of from about 2 to about 600 mg. of active ingredient per kg. of body weight of the subject in one or more applications per day. A preferred daily dosage for adult humans lies in the range of from about 15 to 150 mg. of active ingredient pr kg. of body weight.

The instant compositions may be administered in several unit dosage forms as, for example, in solid or liquid orally ingestible dosage form. The compositions per unit dosage, whether liquid or solid may contain from 0.1% to 99% of active material, the preferred range being from about 10–60%. The composition will generally contain from about 15 mg. to about 1500 mg. of the active ingredient; however, in general, it is preferable to employ a dosage amount in the range of from about 100 mg. to 1000 mg. In parenteral administration the unit dosage is usually the pure compound in a slightly acidified sterile water solution or in the form of a soluble powder intended for solution.

IDENTIFICATION OF STARTING MATERIALS

The compounds of the present invention are conveniently prepared from thienamycin (I) or from the above identified starting material 1. Embodiments of the present invention such as wherein the secondary alcoholic group and/or the carboxyl group are derivatized are conveniently prepared from the corresponding O—, carboxyl, or O- and carboxyl derivatives of thienamycin. Such starting materials are fully disclosed in the following U.S. Patent Applications which are incorporated herein by reference: Ser. No. 733,655 filed Oct. 18, 1976 now abandoned in favor of U.S. patent application Ser. No. 861,234, filed Dec. 16, 1977, now U.S. Pat. No. 4,208,330, issued June 17, 1980, which is directed to O-derivatives of thienamycin (ester and ether derivatives of the secondary alcoholic group of thienamycin) having the following structural formula:

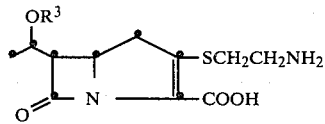

Ia

Ser. No. 733,653 (filed Oct. 18, 1976) now abandoned in favor of U.S. patent application Ser. No. 861,247, filed Dec. 16, 1977, now abandoned in favor of U.S. patent application Ser. No. 160,718, filed June 18, 1980, which is directed to N-acyl derivatives of thienamycin having the following structural formula:

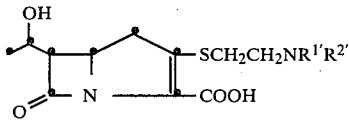

Ib wherein $R^{1'}$ and $R^{2'}$ are selected from the group consisting of hydrogen and acyl; the term "acyl" is defined, as it is in the incorporated by reference application, below.

Ser. No. 733,651 (filed Oct. 18, 1976)now abandoned in favor of U.S. patent application Ser. No. 861,314, filed Dec. 16, 1977, now U.S. Pat. No. 4,181,733, Issued Jan. 1, 1980, which is directed to carboxyl derivatives of thienamycin having the following structural formula:

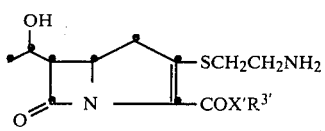

Ic

Ser. No. 733,613 (filed Oct. 18, 1976) now abandoned in favor of U.S. patent application Ser. No. 861,150, filed Dec. 16, 1977, now abandoned in favor of U.S. patent application Ser. No. 160,720, filed June 18, 1980, which is directed to N-acyl and carboxyl derivatives of thienamycin having the structural formula:

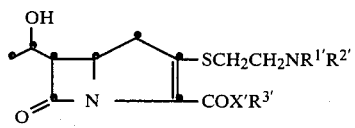

Id

Ser. No. 733,652 (filed Oct. 18, 1976) now abandoned in favor of U.S. patent application Ser. No. 861,246, filed Dec. 16, 1977, now U.S. Pat. No. 4,226,870, issued Oct. 7, 1980, which is directed to N-acyl, O- and carboxyl derivatives of thienamycin having the following structural formula:

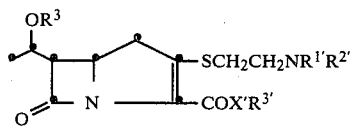

Ie

Thus O- and/or carboxyl derivatized embodiments of the present invention depicted as II, above, may be prepared by starting with the corresponding derivative Ia, Ib, Ic, Id, Ie; or such embodiments may be prepared directly starting with thienamycin, I, (I→II) followed by the desired derivatization procedure to establish $R^3$ and/or $X'R^{3'}$ which is described in the above-cited and incorporated by reference U.S. patent applications.

Relative to structures Ia, Ib, Ic, Id, Ie, as well as II and 1 the radicals $R^3$, $R^{3'}$, $X'$ and acyl ($R^{1'}$ and $R^{2'}$) are defined as follows.

IDENTIFICATION OF THE RADICAL
—COX'R$^{3'}$

In the generic representation of the compounds of the present invention, the radical represented by —Cox'R$^{3'}$ is, inter alia, —COOH (X' is oxygen and $R^{3'}$ is hydrogen) and all radicals known to be effective as pharmaceutically acceptable ester, anhydride ($R^{3'}$ is acyl) and amide radicals in the bicyclic β-lactam antibiotic art, such as the cephalosporins and penicillins and the nuclear analogues thereof.

Suitable radicals ($R^{3'}$) include conventional protecting or carboxyl blocking groups. The term "blocking group" as utilized herein is employed in the same manner and in accordance with the teaching of U.S. Pat. No. 3,697,515 which is incorporated herein by reference. Pharmaceutically acceptable thienamycin derivatives of the present invention falling in this class are given below. Suitable blocking esters thus include those selected from the following list which is representative and not intended to be an exhaustive list of possible ester groups, wherein X'=O and $R^{3'}$ is given:

(i) $R^{3'}=CR^aR^bR^c$ wherein at least one of $R^a, R^b$ and $R^c$ is an electron-donor, e.g., p-methoxyphenyl, 2,4,6-trimethylphenyl, 9-anthryl, methoxy, $CH_2SCH_3$, tetrahydrofur-2-yl, tetrahydropyran-2-yl or fur-2-yl. The remaining $R^a$, $R^b$ and $R^c$ groups may be hydrogen or organic substituting groups. Suitable ester groups of this type include p-methoxybenzyloxycarbonyl and 2,4,6-trimethylbenzyloxycarbonyl.

(ii) $R^{3'}=CR^aR^bR^c$ wherein at least one of $R^a$, $R^b$ and $R^c$ is an electron-attracting group, e.g., benzoyl, p-nitrophenyl, 4-pyridyl, trichloromethyl, tribromomethyl, iodomethyl, cyanomethyl, ethoxycarbonylmethyl, arylsulphonylmethyl, 2-dimethylsulphoniummethyl, o-nitrophenyl or cyano. Suitable esters of this type include benzoylmethoxycarbonyl, p-nitrobenzyloxycarbonyl, 4-pyridylmethoxycarbonyl, 2,2,2-trichloroethoxycarbonyl and 2,2,2-tribromoethoxycarbonyl.

(iii) $R^{3'}=CR^aR^bR^c$ wherein at least two of $R^a$, $R^b$ and $R^c$ are hydrocarbon such as alkyl, e.g., methyl or ethyl, or aryl, e.g. phenyl and the remaining $R^a$, $R^b$ and $R^c$ group, if there is one, is hydrogen. Suitable esters of this type include t-butyloxycarbonyl, t-amyloxycarbonyl, diphenylmethoxycarbonyl and triphenylmethoxycarbonyl.

(iv) $R^{3'}=R^d$, wherein $R^d$ is adamantyl, 2-benzyloxyphenyl, 4-methylthiophenyl or tetrahydropyran-2-yl.

Silyl esters, under this category of blocking groups, may conveniently be prepared from a halosilane or a silazane of the formula:

$R^4_3SiX'$; $R^4_2SiX'_2$; $R^4_3Si.NR^4_2$; $R^4_3Si.NH.COR^4$; $R^4_3Si.NH.CO.NH.SiR^4_3$; $R^4NH.CO.NH^4.SiR^4_3$; or $R^4C(OSiR^4_3)$; $NH(SiR^4_3)_2$ wherein $X'$ is a halogen such as chloro or bromo and the various groups $R^4$, which can be the same or different, represent hydrogen atoms or alkyl, e.g., methyl, ethyl, n-propyl, iso-propyl; aryl, e.g., phenyl; or aralkyl, e.g., benzyl groups.

More generally stated, pharmaceutically acceptable carboxyl derivatives of the present invention are those derived by reacting thienamycin or an N-protected thienamycin, such as N-acylated thienamycin, with alcohols, phenols, mercaptans, thiophenols, acylating reagents and the like. For example, esters and amides of interest are the above-listed starting materils and final products having the following group at the 2-position of the thienamycin nucleus: —$COX'R^{3'}$ wherein $X'$ is oxygen, sulfur, or $NR'$ ($R'$ is H or $R^{3'}$), and R is alkyl having 1-10 carbon atoms, straight or branched, such as methyl, ethyl, t-butyl, pentyl, decyl and the like; carbonylmethyl, including phenacyl, p-bromophenacyl, t-t-butylphenacyl, acetoxyacetylmethyl, pivaloxyacetylmethyl, carboxymethyl, and its alkyl and aryl esters, α-carboxy-α-isopropyl; aminoalkyl including 2-methylaminoethyl, 2-diethylaminoethyl, 2-acetamidoethyl, phthalimidomethyl, succinimidomethyl; alkoxyalkyl wherein the alkoxy portion has 1-10 and preferably 1-6 carbon atoms; but can be branched, straight or cyclic, and the alkyl portion has 1-6 carbon atoms, such as methoxymethyl, ethoxymethyl, isopropoxymethyl, decyloxymethyl, ethoxypropyl, decyloxypentyl, cyclohexyloxymetyl and the like; alkanoyloxyalkyl wherein the alkanoyloxy portion is straight or branched and has 1-6 carbon atoms and the alkyl portion has 16 carbon atoms, such as acetoxymethyl, pivaloyloxymethyl, acetoxyethyl, propionyloxyethyl, acetoxypropyl, and the like; haloalkyl wherein halo is chloro, bromo, fluoro, or iodo, and the alkyl portion is straight or branched having 1-6 carbon atoms, e.e., 2,2,2-trichloroethyl, trifluoroethyl, 2-bromopropyl, diiodomethyl, 2-chloroethyl, 2-bromoethyl, and the like; alkenyl having 1-10 carbon atoms, either straight or branched, e.g., allyl, 2-propenyl, 3-butenyl, 4-butenyl, 4-pentenyl, 2-butenyl, 3-pentenyl, 3-methyl-3-butenyl, metallyl, 1,4-cyclohexadien-1-yl-methyl, and the like alkynyl having 1-10 carbon atoms, either straight or branched e.g., 3-pentenyl, propargyl, ethynyl, 3-butyn-1-yl, and the like; alkanoyl, either straight or branched, having 1-10 carbon atoms, such as pivaloyl, acetyl, propionyl, and the like; aralkyl or heteroarakyl wherein alkyl has 1-3 carbon atoms, and hetero means 1-4 hetero atoms being selected from the group consisting of O, S, or N, such as benzyl, benzhydryl, and substituted benzyl, benzhydryl, or e.g., benzyl or benzhydryl substituted with 1-3 substituents such as benzyl, phenoxy, halo, loweralkyl, loweralkanoyloxy of 1-5 carbon atoms, lower alkoxy, hydroxy, nitro, blocked carboxy, or combinations thereof, e.g., p-chlorobenzyl, o-nitrobenzyl, 3,5-dinitrobenzyl, p-methoxybenzyl, m-benzoylbenzyl, p-t-butylbenzyl, m-phenoxybenzyl, p-benzoylbenzyl, p-nitrobenzyl, 3,5-dichloro-4-hydroxybenzyl, p-methoxycarbonylbenzyl, p-methoxybenzhydryl, p-carboxybenzyl, the latter being either the free acid, ester or the sodium salt, 2,4,6-trimethylbenzyl, p-pivaloyloxybenzyl, p-t-butoxycarbonyl benzyl, p-methylbenzyl, p-benzoyloxybenzyl, p-acetoxybenzyl, p-2-ethylhexanoylbenzoyl, p-ethoxycarbonylbenzyl, p-benzoylthiobenzyl, p-benzamidobenzyl, o-pivaloyloxybenzyl, m-pivaloyloxybenzyl, p-isopropoxybenzyl, p-t-butoxybenzyl, as well as the cyclic analogues thereof, 2,2-dimethyl-5-coumaranmethyl, 5-indanylmethyl, p-trimethylsilylbenzyl, 3,5-bis-t-butoxy-4-hydroxybenzyl; 2-thienylmethyl, 2-furylmethyl, 3-t-butyl-5-isothiazolmethyl, 6-pivaloyloxy-3-pyridazinylethyl, 5-phenylthio-1-tetrazolymethyl, or the like (the use of the terms lower alkyl or lower alkoxy in this context means 1-4 carbon atoms chain); or phthalidyl; or phenylethyl, 2-(p-methylphenyl)-ethyl, and the arylthioalkyl analogues, aryloxyalkyl wherein aryl is preferably a phenyl ring a having 0-3 substituents preferably 0 or 1 substituents in the ortho or para positions and alkyl is 1-6 carbon atoms; e.g., (4-methoxy)-phenoxymethyl, phenoxymethyl, (4-chloro)phenoxymethyl, (4-nitro)phenoxymethyl, (4-benzyloxy)phenoxymethyl, (4-methyl)-phenoxymethyl, (4-benzyloxy)phenoxymethyl, (4-methyl)phenoxymethyl, (2-methoxy)phenoxymethyl, (1-phenoxy)ethyl, (4-amino)phenoxymethyl, (4-methoxy)phenylthiomethyl, (4-chloro)phenylthiomethyl, phenylthioethyl; aryl wherein aryl is phenyl, 5-indanyl, or substituted phenyl having 0-3 substituents, preferably 0 or 1 substituent in the ortho or para position, e.g. (4-methyl)phenyl, (4-hydroxy)-phenyl, (4-t-butyl)phenyl, p-nitrophenyl, 3,5-dinitrophenyl, or p-carboxyphenyl, the latter having either the free acid or the sodium salt form; aralkenyl wherein aryl is phenyl and alkenyl has 1-6 carbon atoms, such as 3-phenyl-2-propenyl; aralkoxyalkyl wherein aralkoxy is benzyloxy, and alkyl has 1-3 carbon atoms, such as benzyloxymethyl, (4-nitro)-benzyloxymethyl, (4-chloro)benzyloxymethyl; alkylthioalkyl wherein the alkylthio portion has 1-10 and preferably 1-6 carbon atoms, but can be branched, straight or cyclic, and the alkyl portion has 1-6 carbon atoms, such as methylthioethyl, ethylthioethyl, cyclohexylthiomethyl, decylthiobutyl, methylthiopropyl, isopropylthioethyl, methylthiobutyl and the like.

In addition to the esters (and thio esters) listed above, amides are also embraced by the present invention, i.e., wherein X' is the

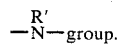group.

Representative of such amides are those wherein R' is selected from the group consisting of hydrogen, methyl, ethyl, phenyl, p-methoxyphenyl, benzyl, carboxymethyl, methylthioethyl, and heteroaryl; also embraced by —COX'R$^{3'}$ are anhydrides wherein R$^{3'}$ is acyl, for example, benzyloxycarbonyl, ethoxycarbonyl, benzoyl, and pivaloyl.

The most preferred —COX'R$^{3'}$ radicals of the present invention are those wherein (relative to Structure II, above) X' is oxygen, sulphur or NR' (R' is selected from the group consisting of hydrogen and lower alkyl); and R$^{3'}$ is selected from the group consisting of: loweralkyl, lower alkenyl, such as methallyl, 3-methylbutenyl, 3-butenyl, and the like; methylthioethyl; benzyl and substituted benzyl such as p-t-butylbenzyl, m-phenoxybenzyl, p-pivaloyloxybenzyl, p-nitrobenzyl and the like; pivaloyloxymethyl, 3-phthalidyl and acetoxymethyl, propionyloxymethyl, acetylthiomethyl, pivaloylthiomethyl, allyl, 4-butenyl, 2-butenyl, 3-methyl-2butenyl, phenacyl, acetoxyacetylmethyl, methoxymethyl, p-acetoxybenzyl, p-pivaloyloxybenzyl, p-isopropoxybenzyl, 5-indanylmethyl, 5-indanyl, benzyloxymethyl, ethylthioethyl, methylthiopropyl, methoxycarbonyloxymethyl, ethoxycarbonyloxymethyl, dimethylaminoacetoxymethyl, crotonolacton-3-yl, and acetamidomethyl.

Identification of R$^3$(R$^{1'}$ and R$^{2'}$)

In the generic representation of the present invention, structure II (above), the radical R$^3$ is, in addition to hydrogen, 1.) acyl (generically the group —OR$^3$ is classifiable as an ester); or 2.) R$^3$ is selected from alkyl, aryl, aralkyl, and the like such that the group —OR$^3$ is classifiable as an ether. For the ester embodiments (1) R$^3$ is selected from the following definition of acyl radicals (p=1). In the so-called ether embodiments (2.) of the present invention, R$^3$ is selected from the same acyl radicals wherein the carbonyl moiety.

, or more generally

, is deleted (p=0); thus R$^3$ is selected from the following radicals wherein all symbolism is defined below:

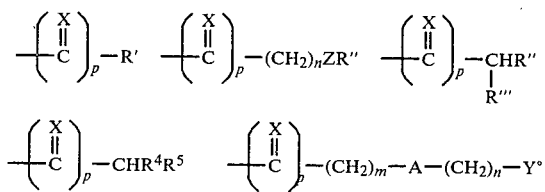

R$^{1'}$ and R$^{2'}$ are selected from the above radicals wherein p=1. Thus, relative to the definition of R$^3$, R$^{1'}$ and R$^{2'}$, the acyl radical can, inter alia, be substituted or unsubstituted aliphatic, aromatic or heterocyclic, araliphatic or heterocyclylaliphatic carboxylic acid radical, a substituted or unsubstituted carbamyl radical or a carbothioic acid radical. One group of acyl radicals can be represented by the general formula:

wherein X is O or S and R" represents hydrogen; amino; substituted amino such as alkyl- and dialkylamino wherein the alkyl radical comprises 1 to about 6 carbon atoms; substituted or unsubstituted: straight or branched chain allyl wherein the alkyl radical comprises 1 to about 6 carbon atoms; mercapto aryloxy, typically comprising 6 to 10 carbon atoms; alkenyl, or alkynyl groups typically comprising 2 to 6 carbon atoms; aryl such as phenyl; aralkyl such as benzyl; cycloalkyl, typically comprising 3 to 6 carbon atoms; or a heteroaryl or heteroaralkyl group (mono- and bicyclic) wherein the alkyl moiety typically comprises 1 to 3 carbon atoms and the heterocyclic ring comprises typically 4 to 10 atoms and the hetero atom or atoms are selected from O, N and S; such above-listed groups can be unsubstituted or can be substituted by radicals such as OH, SH, SR (R is lower alkyl or aryl such as phenyl, alkyl or alkoxy groups having 1 to about 6 carbon atoms, halo, such as Cl, Br, R and I, cyano, carboxy, sulfamino, carbamoyl, sulfonyl, azido, amino, substituted amino such as alkylamino including quaternary ammonium wherein the alkyl group comprises 1 to 6 carbon atoms, haloalkyl such as trifluoromethyl, carboxyalkyl, carbamoylalkyl, N-substituted carbamoylalkyl, wherein the alkyl moiety of the foregoing four radicals comprises 1 to about 6 carbon atoms, amidino, guanidino, N-substituted guanidino, guanidino lower alkyl and the like. Representative examples of such acyl groups that might be mentioned are those wherein R" is benzyl, p-hydroxybenzyl, 4-amino-4-carboxybutyl, methyl, cyanomethyl, 2-pentenyl, n-amyl, n-heptyl, ethyl 3- or 4-nitrobenzyl, phenethyl, β,β-diphenylethyl, methyldiphenylmethyl, triphenylmethyl, 2-methoxyphenyl, 2,6-dimethoxyphenyl, 2,4,6-trimethoxyphenyl, 3,5-dimethyl-4-isoxazolyl, 3-butyl-5-methyl-4-isoxazolyl, 5-methyl-3-phenyl-4-isoxazolyl, 3-(2-chlorophenyl)-5-methyl-4-isoxazolyl, 3-(2,6-dichlorophenyl)5-methyl-4-isoxazolyl, D-4-amino-4-carboxybutyl, D-4 N-benzoylamino-4-carboxy-n-butyl, p-aminobenzyl, o-aminobenzyl, m-aminobenzyl, p-dimethylaminobenzyl, (3-pyridyl)methyl, 2-ethoxy-1-napthyl, 3-carboxy-2-quinoxalinyl, 3-(2,6-dichlorophenyl)-5-(2-furyl)-4-isoxazolyl, 3-phenyl-4-isoxazolyl, 5-methyl-3-(4-guanidinophenyl)4-isoxazolyl, 4-guanidinomethylphenyl, 4-guanidinomethylbenzyl, 4-guanidinobenzyl, 4-guanidinophenyl, 2,6-dimethoxy-4-guanidino, o-sulfobenzyl, p-carboxymethylbenzyl, p-carbamoylmethylbenzyl, m-fluorobenzyl, m-bromobenzyl, p-chlorobenzyl, p-methoxybenzyl, 1-naphthylmethyl, 3-isothiazolylmethyl, 4-isothiazolylmethyl, 5-isothiazolylmethyl, guanylthiomethyl, 4-pyridylmethyl, 5-isoxazolylmethyl, 4-methoxy-5-isoxazolylmethyl, 4-methyl-5-isoxazolylmethyl, 1-imidazolylmethyl, 2-benzofuranylmethyl, 2-indolylmethyl, 2-phenylvinyl, 2-phenylethynyl, 1-aminocyclohexyl, 2- and 3- thienylaminomethyl, 2-(5-nitrofuranyl)-vinyl, phenyl, o-methoxyphenyl, o-chlorophenyl, o-phenylphenyl, p-aminomethylbenzyl, 1-(5-cyanotriazolyl)methyl, difluoromethyl, dichloromethyl, dibromomethyl, 1-(3-methylimidazolyl)methyl, 2- or 3-(5-carboxymethylthienyl)methyl, 2- or 3-(4-carbamoylthienyl)methyl, 2- or 3-(5-methylthienyl)methyl, 2- or 3-(methoxythienyl)methyl, 2- or 3-(4-chlorothienyl)methyl, 2- or 3-(5-sulfothienyl)methyl, 2- or 3-(5-carboxythienyl)methyl, 3-(1,2,5-thiadiazolyl)methyl, 3-(4-methoxy-1,2,5-thiadiazolyl)methyl, 2-furylmethyl, 2-(5-nitrofuryl)methyl, 3-furylmethyl, 2-thienylmethyl, 3-thienylmethyl, tetrazolylmethyl, benzamidinomethyl and cyclohexylamidinomethyl.

The acyl group can also be a radical of the formula:

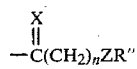

wherein X is O or S and n is 0–4, Z represents oxygen, sulfur, carbonyl or nitrogen and R" is defined as above. Representative members of the substituent

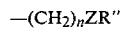

that might be mentioned are allylthiomethyl, phenylthiomethyl, butylmercaptomethyl, α-chlorocrotylmercaptomethyl, phenoxymethyl, phenoxyethyl, phenoxybutyl, phenoxybenzyl, diphenoxymethyl, dimethylmethoxyethyl, dimethylbutoxymethyl, dimethylphenoxymethyl, 4-guanidinophenoxymethyl, 4-pyridylthiomethyl, p-(carboxymethyl)phenoxymethyl, p-(carboxymethylphenylthiomethyl, 2-thiazolylthiomethyl, p-(sulfo)phenoxymethyl, p-(carboxymethyl)phenylthiomethyl, 2-pyrimidinylthiomethyl, phenethylthiomethyl, 1-(5,6,7,8-tetrahydronaphthyl)oxomethyl, N-methyl-4-pyridylthio, benzyloxy, methoxy, ethoxy, phenoxy, phenylthio, amino, methylamino, dimethylamino, pyridinium methyl, trimethylammoniummethyl, cyanomethylthiomethyl, trifluoromethylthiomethyl, 4-pyridylethyl, 4-pyridylpropyl, 4-pyridylbutyl, 3-imidazolylethyl, 3-imidazolylpropyl, 3-imidazolylbutyl, 1-pyrroloethyl, 1-pyrrolopropyl, and 1-pyrrolobutyl.

Alternatively, the acyl group can be a radical of the formula:

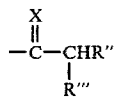

wherein R" is defined as above and R''' is a radical such as amino, hydroxy, azido, carbamoyl, guanidino, amidino, acyloxy, halo, such as Cl, F. Br, I, sulfamino, tetrazolyl, sulfo, carboxy, carbalkoxy, phosphono and the like. Representative members of the substituent

that might be mentioned are α-aminobenzyl, α-amino-(2-thienyl)methyl, α-(methylamino)benzyl, α-aminomethylmercaptopropyl, α-amino-3- or 4-chlorobenzyl, α-amino-3- or 4-hydroxybenzyl, α-amino-2,4-dichlorobenzyl, α-amino-3,4-dichlorobenzyl, D(−)-α-hydroxybenzyl, α-carboxybenzyl, α-amino-(3-thienyl)methyl D(−)-α-amino-3-chloro-4-hydroxybenzyl, α-amino(cyclohexyl)methyl, α-(5-tetrazolyl)benzyl, 2-thienyl-carboxymethyl, 3-thienyl-carboxymethyl, 2-furylcarboxymethyl, 3-furyl-carboxymethyl, α-sulfaminobenzyl, 3-thienyl-sulfaminomethyl, α-(N-methylsulfamino)-benzyl D(−)-2-thienyl-guanidinomethyl, D(−)-α-guanidinobenzyl α-guanylureidobenzyl, α-hydroxybenzyl, α-azidobenzyl, α-fluorobenzyl, 4-(5-methoxy-1,3-oxadiazolyl)-aminomethyl, 4-(5-methoxy-1,3-oxadiazolyl)-hydroxymethyl, 4-(5-methoxy-1,3-sulfadiazolyl)-hydroxymethyl, 4-(5-chlorothienyl)-aminomethyl, 2-(5-chlorothienyl)-hydroxymethyl, 2-(5-chlorothienyl)-carboxy-methyl, 3-(1,2-thiazolyl)-aminomethyl, 3-(1,2-thiazolyl)-hydroxymethyl, 3-(1,2-thiazolyl)-carboxymethyl, 2-(1,4-thiazolyl)-aminomethyl, 2-(1,4-thiazolyl)-hydroxymethyl, 2-(1,4-thiazolyl)carboxymethyl, 2-benzothienylaminomethyl, 2-benzothienylhydroxymethyl, 2-benzothienylcarboxymethyl, α-sulfobenzyl, α-phosphonebenzyl, α-diethylphosphono, and α-monoethylphosphono. Further acyl radicals of interest in this class when X=oxygen are:

wherein $R^4$ and $R^5$ are as defined below. $R^4$ represents hydrogen, halo, such as chloro, fluoro, bromo, iodo, amino, guanidino, phosphono, hydroxy, tetrazolyl, carboxy, sulfo, or sulfamino and $R^5$ represents phenyl, substituted phenyl, a mono- or bicyclic heterocyclyl containing one or more oxygen, sulfur or nitrogen atoms in the ring, such as furyl, quinoxalyl, thienyl, quinolyl, quinazolyl, thiazolyl, siothiazolyl, tetrazolyl, oxadiazolyl, thiadiazolyl and and the like substituted heterocycles, phenylthio, phenyloxy lower alkyl of 1–6 carbon atoms, heterocyclic or substituted heterocyclic thio groups; or cyano. The substituents on the moieties, $R^4$ and $R^5$, can be halo, carboxymethyl, guanidino, guanidinomethyl, carboxamidomethyl, aminomethyl, nitro, methoxy or methyl. When $R^4$ is selected from the group consisting of hydrogen, hydroxy, amino or carboxy and $R^5$ is selected from the group consisting of phenyl, or a 5- or 6-membered heterocyclic ring having one or two sulfur, oxygen or nitrogen hetero atom such as tetrazolyl, thienyl, furyl and phenyl, the following acyl radicals are representative: phenylacetyl 3-bromophenylacetyl, p-aminomethylphenylacetyl, 4-carboxymethylphenylacetyl, 4-carboxyamidomethylphenylacetyl, 2-furylacetyl, 5-nitro-2-furylacetyl, 3-furylacetyl, 2-thienylacetyl, 5-chloro-2-thienylacetyl, 5-methoxy-2-thienylacetyl, α-guanidino-2-thienylacetyl, 3-thienylacetyl, 2-(4-methylthienyl)acetyl, 3-isothiazolylacetyl, 4-methoxy-3-isothiazolylacetyl, 4-isothiazolylacetyl, 3-methyl-4-isothiazolylacetyl, 5-isothiazolylacetyl, 3-chloro-5-isothiazolylacetyl, 3-methyl-1,2,5-oxadiazolylacetyl, 1,2,5-thiadiazolyl-4-acetyl, 3-methyl-1,2,5-thiadiazolylacetyl, 3-chloro-1,2,5-thiadiazolylacetyl, 3-methoxy-1,2,5-thiadiazolylacetyl, phenylthioacetyl, 4-pyridylthioacetyl, cyanoacetyl, 1-tetrazolylacetyl, α-fluorophenylacetyl, D-phenylglycyl, 4-hydroxy-D-phenylglycyl, 2-thienylglycyl, 3-theinylglycyl, phenylamlonyl, 3-chlorophenylmalonyl, 2-thienylmalonyl, 3-thienylmalonyl, α-phosphonophenylacetyl, α-amino cyclohexadienylacetyl, α-sulfaminophenylacetyl, α-hydroxyphenylacetyl, α-tetrazolylphenylacetyl and α-sulfophenylacetyl.

The acyl radical may also be selected from sulphur (1) and phosphorus (2) radicals:

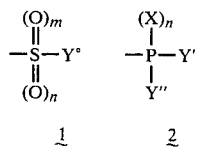

wherein with respect to 1, m and n are integers selected from 0 or 1 and $Y°=O^{\ominus}M^{\oplus}$, $-N(R'')_2$, and $R''$; wherein $M^{\oplus}$ is selected from hydrogen; alkyl metal cations and organic bases; and $R''$ is as defined above, e.g., alkyl, alkenyl, aryl and heteroaryl. With respect to 2 X=O or S; n=0 or 1; and Y' and Y'' are selected from the group consisting of $O^{\ominus}M^{\oplus}$, $-N(R'')_2$, $R''$ and $ZR''$ wherein all symbolism is as defined above, e.g., $R''$ and $ZR''$ are respectively alkyl, alkenyl, aryl, heteroaryloxy, Y' and Y''', including $R''$ moieties, can be joined together to form cyclic ester, ester-amide and amide functions. Illustrative examples of 1 are O-(methylsulphonyl)theinamycin, O-(p-nitrophenylsulphonyl)thienamycin, O-(p-chlorophenylsulphinyl)thienamycin, O-(o-nitrophenylsulphenyl)thienamycin, O-sulfamoylthienamycin, O-dimethylsulphamoylthienamycin and thienamycin O-sulphonic acid sodium salt. Illustrative examples of 2 are O-(dimethoxyphosphino)thienamycin, O-(dibenzyloxyphosphino)thienamycin, O-(dihydroxyphosphino)thienamycin disodium salt, O-(dimethoxyphosphinyl)thienamycin, O-(dimethoxyphosphinothionyl)thienamycin, O-(dibenzyloxyphosphinyl)thienamycin, and O-(dihydroxyphosphinyl)thienamycin disodium salt. The definition of $R^{1'}$ and $R^{2'}$ does not embrace radicals 1 and 2.

An acyl class of particular interest is those acyl radicals which are selected from the group consisting of conventionally known N-acyl blocking or protective groups such as carbobenzyloxy, ring-substituted carbobenzyloxy such as o- and p-nitrocarbobenzyloxy, p-methoxycarbobenzyloxy, chloroacetyl, bromoacetyl, phenylacetyl, t-butoxycarbonyl, trifluoroacetyl, bromoethoxycarbonyl, 9-fluorenylmethoxycarbonyl, dichloroacetyl, o-nitrophenylsulfenyl, 2,2,2-trichloroethoxycarbonyl, bromo-t-butoxycarbonyl, phenoxyacetyl, non-acyl protective groups such as trilower alkyl silyl, for example, trimethylsilyl and t-butyldimethyl are also of interest.

The following radicals, according to the foregoing definition of acyl, are especially preferred for $R^3$ of structure IIa: formyl, acetyl, propionyl, butyryl, chloroacetyl, methoxyacetyl, aminoacetyl, methoxycarbonyl, ethoxycarbonyl, methylcarbamoyl, ethylcarbamoyl, phenylthiocarbonyl, 3-aminopropionyl, 4-aminobutyryl, N-methylaminoacetyl, N,N-dimethylamino-acetyl, N,N,N-trimethylaminoacetyl, 3-(N,N-dimethyl)-aminopropionyl, 3-(N,N,N-trimethyl)aminopropionyl, N,N,N-triethylaminoacetyl, pyridiniumacetyl, guanidinoacetyl, 3-guanidinopropionyl, $N^3$-methylguanidinopionyl, hydroxyacetyl, 3-hydroxypropionyl, acryloyl, propynoyl, malonyl, phenoxycarbonyl, amidinoacetyl, acetamidincacetyl, amidinopropionyl, acetamidinopropionyl, guanylureidoacetyl, guanylcarbamoyl, carboxymethylaminoacetyl, sulfoacetylaminoacetyl, phosphonoacetylaminoacetyl, $N^3$-dimethylaminoacetamidinopropionyl, ureidocarbonyl, dimethylaminoguanylthioacetyl, 3-(1-methyl-4-pyridinium)propionyl, 3-(5-aminoimidazol-1-yl)propionyl, 3-methyl-1-imidazoliumacetyl, 3-sydnonylacetyl, o-aminomethylbenzoyl, o-aminobenzoyl, sulfo, phosphono,

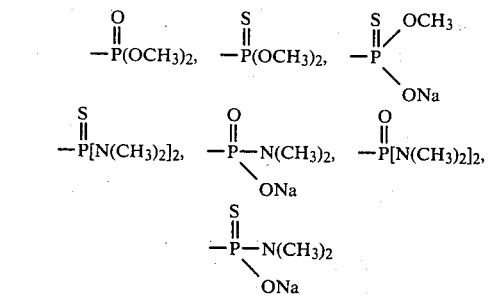

Another class of acyl radicals are thermally substituted acyls wherein the substituent is a basic group such as substituted and unsubstituted: amino, amidino, guanidino, guanyl and nitrogen-containing mono- and bicyclic heterocycles (aromatic and non-aromatic) wherein the hetero atom or atoms, in addition to nitrogen, are selected from oxygen and sulphur. Such substituted acyls may be represented by the following formula:

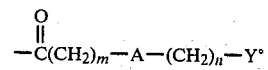

wherein m, and n are integers selected from 0 to 5; A is O, NR' (R' is hydrogen or loweralkyl having 1–6 carbon atoms), S or A represents a single bond; and Y° is selected from the following group:

(1.) amino or substituted amino:

$-N(R°)_2$ and $-N^+(R°)_3$ wherein the values for R° are independently selected from: hydrogen; $N(R')_2$ (R' is hydrogen or loweralkyl having 1–6 carbon atoms); loweralkyl and loweralkoxyl having from 1 to 6 carbon atoms; loweralkoxyloweralkyl wherein the alkoxy moiety comprises 1 to 6 carbon atoms and the alkyl moiety comprises 2–6 carbon atoms; cycloalkyl and cycloalkylalkyl wherein the cycloalkyl moiety comprises 3–6 carbon atoms and the alkyl moiety comprises 1–3 carbon atoms, two R° groups may be joined together with the N atom to which they are attached to form a ring having 3–6 atoms.

(2.) amidino and substituted amidino:

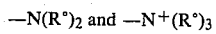

wherein the value of R° is independently selected from the group consisting of: hydrogen; $N(R')_2$ (R' is hydrogen or loweralkyl having 1–6 carbon atoms); loweralkyl and loweralkoxyl having from 1 to 6 carbon atoms, loweralkoxyloweralkyl wherein the alkoxyl moiety comprises 1 to 6 carbon atoms and the alkyl moiety comprises 2 to 6 carbon atoms (when the loweralkoxyloweralkyl radical is attached to carbon the alkyl moiety comprises 1 to 6 carbon atoms); cycloalkyl and cycloalkylalkyl wherein the alkyl moiety comprises 1 to 3 carbon atoms; two R groups may be joined together with the atoms to which they are attached to form a ring having 3 to 6 atoms;

(3.) guanidino and substituted guanidino:

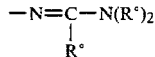

wherein R° is as defined in 2. (above).

(4.) guanyl and substituted guanyl:

wherein R° is as defined in 2. (above).

(5.) nitrogen-containing mono- and bicyclic heterocyclyls (aromatic and non-aromatic) having 4 to 10 nuclear atoms wherein the hetero atom or atoms, in addition to nitrogen, are selected from oxygen and sulphur. Such heterocyclyls are representatively illustrated by the following list of radicals (R' is N or loweralkyl having 1-6 carbon atoms):

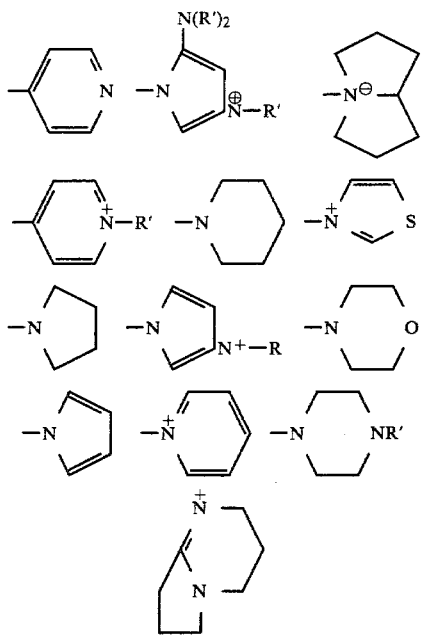

The following specific acyl radicals falling within this class are additionally representative:

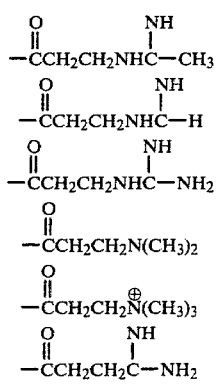

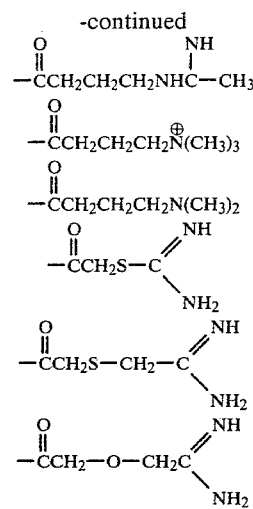

Preparation of Starting Materials Ia, Ib, Ic, Id and Ie

The above-described starting materials are conveniently prepared from an N-protected thienamycin such as an N-acylated thienamycin (2).

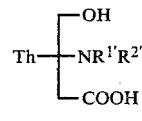

wherein $R^{1'}$ and $R^{2'}$ are selected from hydrogen and the above-defined acyl radicals. Preferably $R^{1'}$ is hydrogen and $R^{2'}$ is an easily removable blocking group such as: carbobenzyloxy, ring-substituted carbobenzyloxy such as o- and p-nitrocarbobenzyloxy, p-methoxycarbobenzyloxy, chloroacetyl, bromoacetyl, phenylacetyl, t-butoxycarbonyl trifluoroacetyl, bromoethoxycarbonyl, 9-fluoroenylmethoxycarbonyl, dichloroacetyl, o-nitrophenylsulfenyl, 2,2,2-trichloroethoxycarbonyl, bromo-t-butoxycarbonyl, phenoxyacetyl; non-acyl protective groups such as triloweralkylsilyl, for example, trimethylsilyl, and t-butyldimethylsilyl are also of interest. The most preferred N-blocking groups are the substituted and unsubstituted carbobenzyloxy radical:

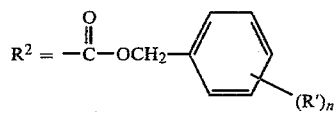

wherein n is 0–2 (n=0, R'=hydrogen) and R' is lower alkoxy or nitro; and bromo-t-butoxycarbonyl,

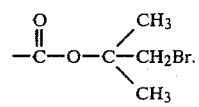

The ultimate N-deblocking procedure for the preparation of Ia, Ic or Ie is accomplished by any of a variety of well-known procedures which include hydrolysis or hydrogenation; when hydrogenation is employed suitable conditions involve a solvent such as a loweralkanoyl in the presence of a hydrogenation catalyst such as palladium, platinum or oxides thereof.

The N-acylated intermediate [2, (or Ia) above] is prepared by treating thienamycin (I) with an acylating agent, for example, an acyl halide or acyl anhydride such as an aliphatic, aromatic, heterocyclic, araliphatic or heterocyclic aliphatic carboxylic acid halide or anhydride. Other acylating agents may also be employed, for example, mixed carboxylic acid anhydrides and particularly lower alkyl esters of mixed carboxylic-carbonic anhydrides; also, carboxylic acids in the presence of a carbodiimide such as 1,3-dicyclohexylcarbodiimide, and an activated ester of a carboxylic acid such as the p-nitrophenyl ester.

Such N-acylated thienamycin starting materials are fully described in co-pending, concurrently filed U.S. patent application Ser. No. 733,653 filed Oct. 18, 1976. This application is incorporated herein by reference.

The acylation reaction may be conducted at a temperature in the range of from about $-20°$ to about $100°$ C., but is preferably conducted at a temperature in the range of from $-9°$ C. to $25°$ C. Any solvent in which the reactants are soluble and substantially inert may be employed, for example polar solvents such as water, alcohols and polar organic solvents in general such as dimethylformamide (DMF), hexamethyl, phosphoramide (HMPA), acetone, dioxane tetrahydrofuran (THF), acetonitrile, heterocyclic amines such as pyridine, ethylacetate, aqueous mixtures of the above, as well as halogenated solvents such as methylene chloride and chloroform. The reaction is conducted for a period of time of from about five minutes to a maximum of three hours, but in general, a reaction time of about 0.5 to about one hour is sufficient. The following equation illustrates this process employing a carboxylic acid halide; however, it is to be understood that by substituting a carboxylic acid anhydride or other functionally equivalent acylating agent similar products may be obtained.

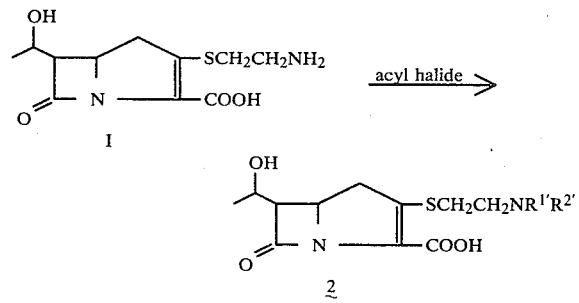

Generally when the above-described acylating reaction employs an acid halide (suitable halides are chloro, iodo, or bromo) or anhydride the reaction is conducted in water or an aqueous mixture of a polar organic solvent such as acetone, dioxane, THF, DMF, acetonitrile or the like in the presence of a suitable acceptor base such as $NaHCO_3$, MgO, NaOH, $K_2HPO_4$ and the like.

In carrying out the reactions described herein, it is generally not necessary to protect the 2-carboxy group or the 1'-hydroxy group; however, in cases where the acylating reagent is exceedingly water sensitive it is sometimes advantageous to perform the acylation in a non aqueous solvent system. Triorganosilyl (or tin) derivatives of thienamycin proceeds rapidly to give the tris-triorganosilyl derivative, for example tris-trimethylsilyl thienamycin

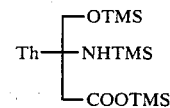

Such derivatives, which are readily soluble in organic solvents, are conveniently prepared by treating thienamycin with an excess of hexamethyldisilazane and a stoichiometric amount of trimethylchlorosilane at $25°$ C., with vigorous stirring under a $N_2$ atmosphere. The resulting $NH_4Cl$ is removed by centrifugation and the solvent is removed by evaporation to provide the desired silyl derivative.

The intermediate starting materials Ic are prepared according to the following scheme; however, it should be noted that direct esterification, without protection of the amino group, is also possible.

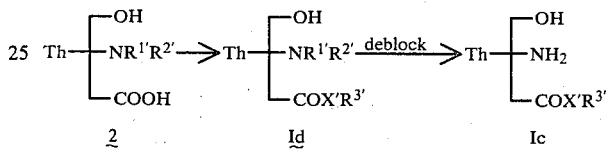

wherein all symbolism is as previously defined.

In general, the transformation (2→Ic) is accomplished by conventional procedures known in the art. Such procedures include:

(1.) Reaction of 2 (or I) with a diazoalkane such as diazomethane, phenlydiazomethane, diphenyldiazomethane, and the like, in a solvent such as dioxane, ethylacetate, acetonitrile and the like at a temperature of from $0°$ C. to reflux for from a few minutes to 2 hours.

(2.) Reaction of an alkali metal salt of 2 with an activated alkyl halide such as methyliodide, benzyl bromide, or m-phenoxybenzyl bromide, p-t-butylbenzyl bromide, pivaloyloxymethyl chloride, and the like. Suitable reaction conditions include solvents such as hexamethylphosphoramide and the like at a temperature of from $0°$ C. to $60°$ C. for from a few minutes to 4 hours.

(3.) Reaction of 2 with an alcohol such as methanol, ethanol, benzyl alcohol, and the like. This reaction may be conducted in the presence of a carbodiimide condensing agent such as dicyclohexylcarbodiimide or the like. Suitable solvent, at a temperature of from $0°$ C. to reflux for from 15 minutes to 18 hours, include $CHCl_3$, $CH_3CH$, $CH_2Cl_2$ and the like.

(4.) Reaction of an N-acylated acid anhydride of 2 prepared by reacting the free acid 2 with an acid chloride such as ethylchloroformate, benzylchloroformate and the like, with an alcohol such as those listed in (3.) under the same conditions of reaction as given above for (3.). The anhydride is prepared by reacting 2 and the acid chloride in a solvent such as tetrahydrofuran (THF), $CH_2Cl_2$ and the like at a temperature of from $25°$ C., to reflux for from 15 minutes to 10 hours.

(5.) Reaction of lable esters of 2 such as the trimethylsilyl ester, dimethyl-t-butylsilyl ester or the like with $R^{3'}X°$ wherein $X°$ is halogen such as bromo and chloro and $R^{3'}$ is as defined, in a solvent such as THF, $CH_2Cl_2$ and the like at a temperature of from $0°$ C. to reflux for from 15 minutes to 16 hours. For example according to the following scheme:

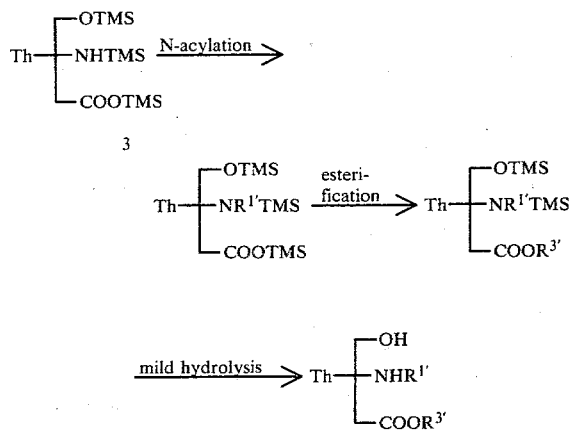

wherein TMS is triorganosilyl such as trimethylsilyl and all other symbolism is as previously defined.

The amides of the present invention are most conveniently prepared by reacting the acid anhydride (Ic, $X'=O$, $R^{3'}=$acyl) with ammonia or with the amine of choice, e.g., the alkyl-, dialkyl-, aralkyl- or heterocyclic amines listed above.

The above-recited schemes of esterification are well known in the related bicyclic β-lactam antibiotic art and indeed in all of general organic synthesis and it is to be noted that there is no undue criticality of reaction parameters in the preparation of the N-acylated and carboxyl derivatives Ic useful as starting materials in the practice of the present invention.

Starting materials Ia and Ie are conveniently prepared by any of a variety of well-known esterification or etherification reactions upon the secondary alcoholic group of Id. Such procedures include:

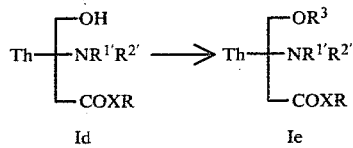

(1.) For the preparation of ether embodiments of the present invention, the acid catalized reaction of Id with a diazoalkane such as diazomethane, phenyldiazomethane, diphenyldiazomethane and the like in an inert solvent such as dioxane, tetrahydrofuran (THF), halohydrocarbons such as $CH_2Cl_2$, ethylacetate and the like in the presence of a catalytic amount of a strong acid or Lewis acid such as toluenesulfonic acid, trifluoroacetic acid, fluoboric acid, boron trifluoride and the like at a temperature of from $-78°$ C. to $25°$ C. for from a few minutes to 2 hours.

(2.) For the preparation of ether embodiments of the present invention, the reaction of Id with an alkylating agent such as active halides, for example methyliodide, benzylbromide, m-phenoxybenzylbromide and the like; alkylsulphonates such as dimethylsulphate, diethylsulphate, methylfluorosulphonate and the like in the presence of a strong base capable of forming the alcoholate anion of Ib. Suitable bases include alkali and alkaline earth metal oxides and hydrous oxides, alkali metal alkoxides such as potassium, tertiarybutoxide, tertiary amines such as triethylamine, alkali metal alkyls and aryls such as phenyllithium, and alkali metal amides such as sodium amide. Suitable solvents include any inert anhydrous solvent such as t-butanol, dimethylformamide (DMF), THF, hexamethylphosphoramide (HMPA) dioxane and the like at a temperature of from $-78°$ C. to $25°$ C., for from a few minutes to 4 hours.

(3.) For the preparation of ester embodiments, of the present invention, the reaction of Id with any of the above-listed acyl radicals in their acid form. This reaction may be conducted in the presence of a carbodiimide condensing agent such a dicyclohexylcarbodiimide or the like. Suitable solvents include any inert solvent such as $CHCl_3$, $CH_2Cl_2$, DMF, HMPA, acetone, dioxane and the like at a temperature of from $0°$ C. to $60°$ C. for from 15 minutes to 12 hours.

(4.) For the preparation of ester embodiments of the present invention, the reaction of Id with an acyl halide or an acid anhydride, wherein the acyl moiety is described above. Generally, when the above-described acylating reaction employs an acid halide (suitable halides are chloro, iodo, or bromo or acid anhydride) the reaction is conducted in an anhydrous organic solvent such as acetone, dioxane, methylenechloride chloroform, DMF, or the like in the presence of a suitable acceptor base such as $NaHCO_3$, MgO, triethylene, pyridine, and the like at a temperature of from $0°$ C. to $40°$ C. for from 1 to 4 hours.

Suitable acyl halides and anhydrides include: acetic anhydride, bromoacetic anhydride, propionic anhydride, benzoylchloride, phenylacetyl, chloride azidoacetyl chloride, 2-thienylacetyl chloride, 2-, 3- and 4-nicotinyl chloride, p-nitrobenzoyl chloride, 2,6-dimethoxybenzoyl chloride, 4-guanidinophenylacetyl chloride, hydrochloride, methanesulfonyl chloride, dibenzylphosphorochloridate, dimethylthiophosphorochloridate, 2-furoyl, ethyl carbonic anhydride, methylchloroformate, bis(p-nitrobenzyl)phosphorochloridate and the like.

(5.) For the preparation of ester embodiments of the present invention, the reaction of Id with a suitably substituted ketene or isocyanate such as ketene, dimethyl ketene, methylisocyanate, methylisothiocyanate, chlorosulfonyl isocyanate and the like. Suitable solvents include dioxane, tetrahydrofuran, chloroform and the like at a temperature of from $-70°$ C. to $60°$ C. for from 15 minutes to 18 hours.

The intermediate Ie is then N-deblocked as described above to provide starting materials, Ie ($R^{1'}$ and $R^{2'}=H$) and Ia. From Ie, Ia is prepared by deblocking the carboxyl group:

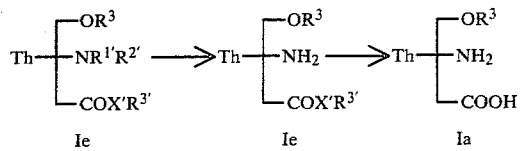

Starting material Ia is conveniently and preferably obtained when $X'$ is oxygen and $R^{3'}$ is a readily removable carboxyl protecting or blocking group (see above). Starting material Ia is prepared by deblocking according to any of a variety of well known procedures which include hydrolysis and hydrogenation. When the preferred carboxyl-blocking groups are employed (below), the preferred deblocking procedure is hydrogenation, wherein the intermediate species (Ie) in a solvent such as a lower alkanoyl, is hydrogenated in the presence of a hydrogenation catalyst such as palladium, platinum or oxides thereof.

In this connection, it is noted that suitable "blocking groups" R3' include the sub-generic groups defined above as aralkyl, haloalkyl, alkanoyloxyalkyl, alkoxyalkyl, alkenyl, substituted alkyl, or aralkoxyalkyl, and also including alkylsilyl, wherein alkyl has 1–10 carbon atoms. For example, suitable "blocking groups" R3' include benzyl, phenacyl, p-nitrobenzyl, methoxymethyl, trichloroethyl, trimethylsilyl, tributyltin, p-methoxybenzyl, benzhydryl. These blocking groups are preferred since they are generally recognized easily-removable blocking groups in cephalosporin and penicillin art.

The preferred carboxyl blocking groups, are benzyl and substituted benzyl:

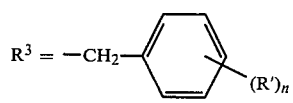

wherein n is 0–2 (n=0, R'=H) and R' is loweralkoxyl or nitro.

In the alternative it should be noted that the compounds of the present invention, II, may be arrived at by operating upon the substituted N-methylene thienamycin derivative, II, to achieve derivatization by establishment of $R^3$ and/or $-COX'R^{3'}$. Such procedures is exactly as described above except that species II replaces the above-described starting materials, such as Ia, Ic and Ie, and, of course, there is no need to N-deblock.

The following examples, illustrate but do not limit the product, process, compositional or method of treatment aspects of the present invention.

EXAMPLE 1

Preparation of N-(3-Azidopropionimidoyl)Thienamycin

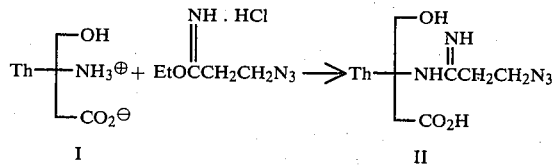

Thienamycin (133 mg) is dissolved in 10 ml pH 7.0, 0.1 M phosphate buffer and cooled in an ice-bath with magnetic stirring. The solution is adjusted to pH 8.5 with 2.5 N sodium hydroxide. While maintaining a pH of 8.5 with sodium hydroxide, O-ethyl 3-azidopropionimidate hydrochloride (1.2 g) is added portionwise over 10 minutes. The mixture is stirred for 0.5 hr, then is neutralized with 2.5 N hydrochloric acid and chromatographed on a Dowex-50W×8 (sodium form) column (4.0×20 cm) which is eluted with water to provide the desired product (II). After lyophilization 30 mg. of the white solid product (II) is obtained.

UV $\lambda_{max}^{H_2O}$ 301 nm; IR (Nujol mull) 2100 cm$^{-1}$ (N$_3$) and 1760 cm$^{-1}$ ($\beta$-lactam) NMR (100 MHz, D$_2$O) $\delta$1.31 (d), 2.78 (t), 3.16 (m), 3.49 (q), 3.66 (m) and 4.20 ppm (m);

Electrophoretic mobility 5 mm toward cathod (at 50 V/cm, for 20 min. in 0.05 M pH 7.0 phosphate buffer).

EXAMPLE 2

Preparation of N-(3-Aminopropionimidoyl)thienamycin (II)

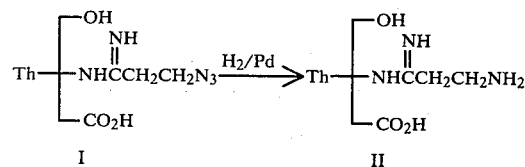

N-(3-Azidopropionimidoyl)thienamycin (I) (43 mg) is dissolved in 40 ml water (pH 7.0) and is hydrogenated under 1 atm of H$_2$ in the presence of 0.1 g Pd catalyst (10% palladium on charcoal) for 30 min. The resulting reaction mixture (pH 9.5) is neutralized with 2.5 N HCl and filtered from the catalyst. The filtrate is concentrated to 10 ml and chromatographed on XAD-2 resin (2.3×16 cm column). The column is eluted with water to provide the desired product (II) (23 mg) as hydrochloride after lyophilization.

UV $\lambda_{max}^{H_2O}$ 301 nm ($\epsilon$7,080); IR (Nujol mull) 1776 cm$^{-1}$ ($\beta$-lactam); NMR (60 MHz, D$_2$O) 1.30 (d), 2.60–3.72 (m), and 4.18 ppm (m); and electrophoretic mobility 60 mm toward cathod (50 V/cm for 1 hr. in 0.05 M pH 7.0 phosphate buffer.)

EXAMPLE 3

Preparation of N-(3-Acetamidinopropionimidoyl)thienamycin (II)

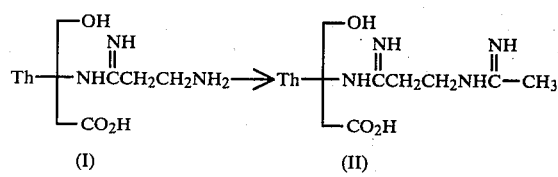

The aqueous solution of N-(3-aminopropionimidoyl)-thienamycin (I) (52 mg) is dissolved in 15 ml water and cooled in an ice-bath with magnetic stirring. The solution is adjusted to pH 8.5 with 2.5 N sodium hydroxide. While maintaining a pH of 8.5 with sodium hydroxide, O-ethyl acetimidate hydrochloride (33 mg) is added portionwise over 10 min. The mixture is stirred for 1 hr. The resulting reaction mixture is neutralized with 2.5 N hydrochloric acid and chromatographed on XAD-2 column (2.5×16 cm) which is eluted with water. Fractions 13–19 (6.5 ml each fraction) are combined and lyophilized to give the desired product (II) (25.5 mg) as hydrochloride.

UV $\lambda_{max}^{H_2O}$ at 301 nm; NMR (100 MHz, D$_2$O) $\delta$2.26 ppm (singlet, acetimidoyl group) and electrophoretic mobility 95 mm toward cathod (at 50 V/cm, for 1 hr. in 0.05 M pH 7.0 phospate buffer).

EXAMPLE 4

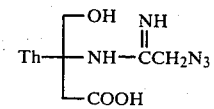

Following the procedure of Example 1, but replacing the reagent with O-ethyl azidoacetimidate, there is obtained: N-(Azidoacetimidoyl)thienamycin

EXAMPLE 5

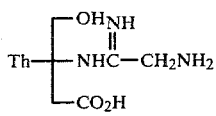

Following the procedure of Example 2, but replacing the starting material with N-(azidoacetimidoyl)thienamycin, there is obtained: N-(aminoacetimidoyl)thienamycin.

EXAMPLE 6

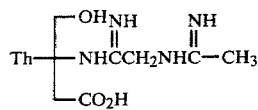

Following the procedure of Example 3, but replacing the starting material with N-(aminoacetimidoyl)thienamycin there is obtained: N-(acetamidinoacetamidoyl)-thienamycin.

EXAMPLE 7

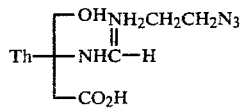

Following the procedure of Example 1, but replacing the reagent with O-ethyl N-(2-azidoethyl)formimidate, there is obtained: N-[N'-(2-azidoethyl)formimidoyl]-thienamycin.

EXAMPLE 8

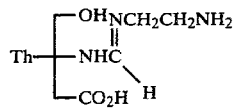

Following the procedure of Example 2, but replacing the starting material with N'-(2-azidoethyl)-N-formimidoylthienamycin, there is obtained: N-[N'-(2-aminoethyl)formimidoyl]thienamycin.

EXAMPLE 9

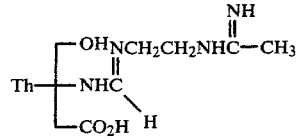

Following the procedure of Example 3, but replacing the starting material with N-[N'-(2-aminoethyl)formimidoyl]thienamycin, there is obtained: N-[N'-(2-acetamidinoethyl)formimidoyl]thienamycin.

EXAMPLE 10

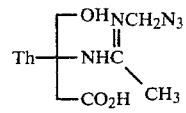

Following the procedure of Example 1, but replacing the reagent with O-ethyl N-(azidomethyl)-acetimidate, there is obtained: N-[N'-(azidomethyl)acetimidoyl]-thienamycin.

EXAMPLE 11

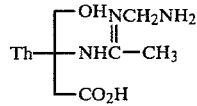

Following the procedure of Example 2, but replacing the starting material with N-[N'-(azidomethyl)acetimidoyl]thienamycin, there is obtained: N-[N'-(aminomethyl)acetimidoyl]thienamycin.

EXAMPLE 12

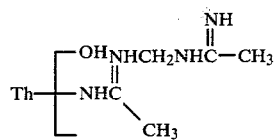

Following the procedure of Example 3, but replacing the starting material with N-[N'-(aminomethyl)acetimidoyl]thienamycin, there is obtained: N-[N'-(acetamidinomethyl)acetimidoyl]thienamycin.

EXAMPLE 13

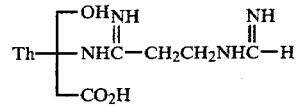

Following the procedure of Example 3, but replacing the reagent with O-methyl formimidate, there is obtained: N-(3-formamidinopropionimidoyl)thienamycin.

EXAMPLE 14

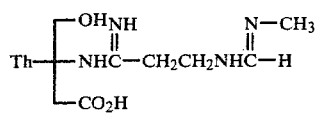

Following the procedure of Example 3, but replacing the reagent with O-ethyl N-methylformimidate, there is obtained: N-[3-(N'-methylformamidino)propionimidoyl]thienamycin.

EXAMPLE 15

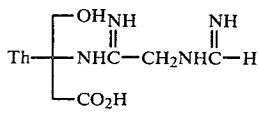

Following the procedure of Example 3, but replacing the starting material and the reagent with N-(aminoacetimidoyl)thienamycin and O-ethyl formimidate, respectively, there is obtained: N-(formamidinoacetimidoyl)thienamycin.

EXAMPLE 16

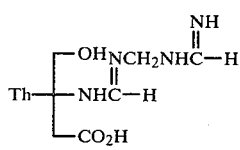

Following the procedure of Example 3, but replacing the starting material and the reagent with N-[N'-(aminomethyl)formimidoyl]thienamycin, and O-ethyl formimidate, respectively, there is obtained: N-[N'-(formamidinomethyl)formimidoyl]thienamycin.

EXAMPLE 17

Preparation of silylated N-(aminoacetimidoyl)thienamycin

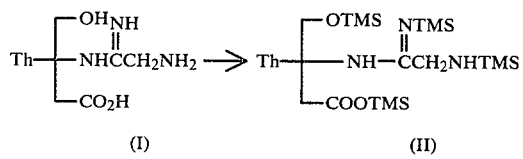

N-(aminoacetimidoyl)thienamycin (I) (80 mg) suspended in 10 ml of dry tetrahydrofuran under a $N_2$ atmosphere is treated with hexamethyldisilazane (1.0 ml) and trimethylchlorosilane (0.3 ml). The mixture is vigorously shaken at 25° C. for 20 min. The suspension is then centrifuged to remove ammonium chloride. The supernatant is evaporated to an oil under a nitrogen stream for further reaction.

EXAMPLE 18

Preparation of N-(N',N'-dimethylformamidinoacetimidoyl)thienamycin

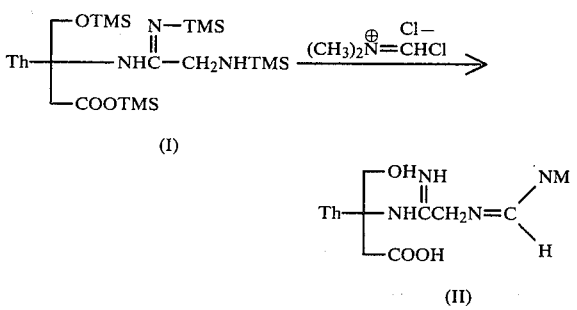

The silylated N-(aminoacetimidoyl)thienamycin (16 mg) in 0.2 ml chloroform is treated with chlorodimethylformiminium chloride (10 mg in 50 μl chloroform) at −20° C. for 1 hr. The mixture is warmed to 25° C. and evaporated to dryness by a nitrogen stream. The residue is redissolved in 0.2 ml THF and treated with 0.5 ml of 0.1 M pH 4.5 phosphate buffer for 20 min. The resulting mixture is chromatographed on a XAD-2 column (2.3×16 cm) which is eluted with water to provide the desired product (II).

EXAMPLE 19

Following the procedure of Example 17, but replacing the starting material, with N-(3-aminopropionimidoyl)thienamycin, there is obtained: silylated N-(3-aminopropionimidoyl)thienamycin.

EXAMPLE 20

Following the procedure of Example 18, but replacing the starting material with silylated N-(3-aminopropionimidoyl)thienamycin, there is obtained: N-[3-(N',N'-dimethylformamidino)propionimidoyl]thienamycin.

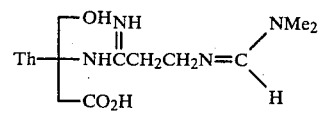

EXAMPLE 21

Preparation of 3-Azidopropionamide

3-Chloropropionamide (50 g) and sodium azide (50 g) are mixed with 160 ml water and 160 ml acetone. The mixture is heated at reflux overnight then is evaporated in vacuo to dryness. The solid residue is extracted with 200 ml ethyl acetate to provide 51 g of the crude product which yields 40 g of white crystalline solids after recrystallization from ether. The ir spectrum of the product showed absorption at 2100 cm$^{-1}$ ($N_3$).

EXAMPLE 22

Preparation of O-ethyl 3-azidopropionimidate fluoroborate

Triethyloxonium fluoroborate (3.0 g) is dissolved in 5.0 ml methylene chloride. To the solution is added 3-azidopropionamide (1.5 g). The mixture is stirred at 25° C. for 2 hrs, then is evaporated in vacuo to give oily product. The crude imidate so obtained is used without further purification.

EXAMPLE 23

Following the procedure of Example 22, but replacing the starting material with azidoacetamide, there is obtained: O-ethyl azidoacetimidate fluoroborate.

EXAMPLE 24

Following the procedure of Example 22, but replacing the starting material with N-methyl-2-azidoacetamide, there is obtained: O-ethyl N-methyl-2-azidoacetimidate fluoroborate.

EXAMPLE 25

Following the procedure set forth in the foregoing text and examples, the following compounds of the present invention are obtained. The reagents, imido ethers and imido halides, utilized in the reaction with thienamycin, or a derivative thereof, to provide the following compounds are either known, or may be prepared as described above.

| Compound | R¹ | R² | R³ | R⁴ | R | R' |
|---|---|---|---|---|---|---|
| (1.) | H | H | H | H | H | —CH₂— |
| (2.) | H | H | H | H | H | —CH₂—CH₂— |
| (3.) | H | H | H | H | H | —CH(CH₃)—CH₂— |
| (4.) | H | H | H | H | H | —CH₂—CH(C₂H₅)— |
| (5.) | H | H | H | H | H | —CH₂CH₂CH₂— |
| (6.) | H | H | H | H | H | —CH₂—O—CH₂— |
| (7.) | H | H | H | H | H | —CH₂—O—CH₂CH₂— |
| (8.) | H | H | H | H | H | —CH₂—S—CH₂CH₂— |
| (9.) | H | H | H | H | H | —CH₂—S—CH₂— |
| (10.) | H | H | H | H | H |  |
| (11.) | H | H | H | H | H | —CH₂— |
| (12.) | H | H | H | H | H | —CH₂——CH₂— |
| (13.) | H | H | H | H | H |  (1,2 & 1,3) |
| (14.) | H | H | H | H | H | —CH₂——CH₂—(1,2 & 1,3) |
| (15.) | H | H | H | H | H | (1,2;1,3) |
| (16.) | H | H | H | H | H | —CH₂—(1,2;1,3) |
| (17.) | H | H | H | H | H | —CH₂—O——CH₂—(1,2;1,3) |
| (18.) | H | H | H | H | H | (1,2;1,3;1,4) |
| (19.) | H | H | H | H | H | —CH₂S—(1,2;1,3;1,4) |
| (20.) | H | H | H | H | H | —CH₂——CH₂—OCH₂—(1,2;1,3;1,4) |
| (21.) | H | H | H | H | H | (o,m-,p-) |
| (22.) | H | H | H | H | H | —CH₂—(o,m-,p-) |
| (23.) | H | H | H | H | H | —CH₂——CH₂—(o-,m-,p-) |
| (24.) | H | H | H | H | H | (2,3;2,4;2,5;2,6) |
| (25.) | H | H | H | H | H | CH₂ (2,3;2,4;2,5;2,6) |
| (26.) | H | H | H | H | H | —CH₂——CH₂ (2,3;2,4;2,5;2,6) |
| (27.) | H | H | H | H | H | —CH₂——CH₂ (2,3;2,4;2,5) |

-continued

| | | | | | | |
|---|---|---|---|---|---|---|
| (28.) | H | H | H | H | H | —CH2—<piperidine>—CH2—(2,3;2,4;2,5) |
| (29.) | H | H | H | H | H | —CH2—<1,3-dioxane>—(2,3;2,5;2,6-) |
| (30.) | H | H | H | H | H | —CH2—<morpholine>—(2,3;2,5;2,6) |
| (31.) | H | H | H | H | CH3 | —CH2— |
| (32.) | H | H | H | CH3 | CH2OCH3 | —CH2CH2— |
| (33.) | H | H | CH3 | CH3 | H | —CH2CH2CH2— |
| (34.) | H | CH3 | H | H | CH3 | —CH2— |
| (35.) | CH3 | CH3 | H | H | H | —CH2— |
| (36.) | H | C2H5 | H | C2H5 | CH2CH3 | —CH2—S—CH2— |
| (37.) | CH3 | CH3 | CH3 | CH3 | CH3 | —CH2— |
| (38.) | H | CH3 | C2H5 | cyclopropyl | H | —CH2— |
| (39.) | H | H | H | CH3 | phenyl | —CH2CH2— |
| (40.) | H | —CH2-phenyl | H | H | H | —CH2-phenyl |
| (41.) | H | H | H | H | CF3 | —CH2— |
| (42.) | H | H | H | H | pyridyl | —CH(CH3)—CH2— |
| (43.) | H | CH3 | H | H | thiazoline | —CH2— |
| (44.) | H | H | H | H | H | —CH2CH2— pyridyl |
| (45.) | H | —CH2CH2SCH3 | R3+R4= piperidino-N | | H | —CH2— |
| (46.) | H | H | H | —CH2CH=CH2 | H | —CH2CH2— |

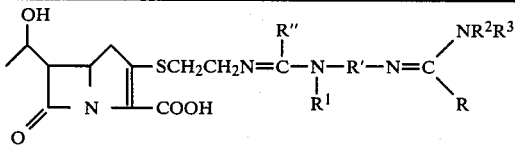

| Compound | R¹ | R² | R³ | R | R' | R'' |
|---|---|---|---|---|---|---|
| (1.) | H | H | H | H | —CH2— | H |
| (2.) | H | H | H | H | —CH2—CH2 | H |
| (3.) | H | H | H | H | —CH2—O—CH2— | H |
| (4.) | H | H | H | H | cyclopropyl-CH2— | H |
| (5.) | H | H | H | H | cyclopentyl-CH2— (1,2;1,3) | H |
| (6.) | H | H | H | H | —CH2-cyclohexyl-CH2SCH2— (1,2;1,3;1,4) | H |
| (7.) | H | H | H | H | —CH2-phenyl-CH2—CH2— (o-;m-;p-) | H |
| (8.) | H | H | H | H | —CH2—CH2— | CH3 |
| (9.) | H | H | H | CH3 | —CH2— | H |
| (10.) | H | H | H | CH3 | —CH2—CH2—CH2— | CH3 |
| (11.) | H | H | CH3 | C2H5 | —CH2—S—CH2— | H |
| (12.) | H | CH3 | C2H5 | H | —CH2— | H |
| (13.) | CH3 | H | H | H | —CH2—CH2— | H |
| (14.) | CH3 | CH3 | CH3 | CH3 | —CH2— | CH3 |
| (15.) | H | H | H | CF3 | —CH2—CH2— | H |

| | | | | | | |
|---|---|---|---|---|---|---|
| (16.) | H | H | H | CH₂—OCH₃ | —CH₂—H | |
| (17.) | H | H | H | —⌬ (phenyl) | —CH₂—CH₂— | H |
| (18.) | H | H | H | piperidinyl-CH | —CH₂—CH₂— | H |
| (19.) | H | H | H | thiazolyl | —CH₂— | H |
| (20.) | H | H | —CH₂—⌬ | H | —CH₂— | H |
| (21.) | H | H | —CH₂CH=CH₂ | H | —CH₂—CH₂— | H |
| (22.) | H | R₂ + R₃ = —N(piperidinyl) | | H | —CH₂ | H |

EXAMPLE 26

Preparation of Pharmaceutical Compositions

One such unit dosage form is prepared by mixing 120 mg. of N-(3-Acetamidinopropionimidoyl)thienamycin with 20 mg of lactose and 5 mg of magnesium stearate and placing the 145 mg mixture into a No. 3 gelatin capsule. Similarly, by employing more of the active ingredient and less lactose, other dosage forms can be put up in No. 3 gelatin capsules and should it be necessary to mix more than 145 mg of ingredients together, larger capsules such as compressed tablets and pills can also be prepared. The following examples are illustrative of the preparation of pharmaceutical formulations:

| TABLET | PER TABLET |
|---|---|
| N-(3-Acetamidinopropionimidoyl) thienamycin | 125 mg. |
| Cornstarch, U.S.P. | 6 mg. |
| Dicalcium Phosphate | 192 mg. |
| Lactose, U.S.P. | 190 mg. |

The active ingredient is blended with the dicalcium phosphate, lactose and about half of the cornstarch. The mixture is then granulated with 15% cornstarch paste (6 mg) and rough-screened. It is dried at 45° C. and screened again through No. 16 screens. The balance of the cornstarch and the magnesium stearate is added and the mixture is compressed into tablets, approximately 0.5 inch in diameter each weighing 800 mg.

| PARENTERAL SOLUTION Ampoule: | |
|---|---|
| N-(3-Acetamidinoprolonimidoyl) thienamycin | 500 mg. |
| Sterile water | 2 ml. |
| OPTHALMIC SOLUTION | |
| N-(3-Acetamidinoproplonimidoyl) thienamycin | 100 mg. |
| Hydroxypropylmethyl Cellulose | 5 mg. |
| Sterile Water | to 1 ml. |
| OTIC SOLUTION | |
| N-(3-Acetamidinoproionimidoyl) thienamycin | 100 mg. |
| Benzalkonium Chlorie | 0.1 mg. |
| Sterile Water | to 1 ml. |

| TOPICAL OINTMENT | |
|---|---|
| N-(3-Acetamidinoproionimidoyl) thienamycin | 100 mg. |
| Polyethylene Glycol 4000 U.S.P. | 400 mg. |
| Polyethylene Glycol 400 U.S.P. | 1.0 gram |

The active ingredient in the above formulations may be administered alone or in combination with other biologically active ingredients as, for example, with other antibacterial agents such as lincomycin, a penicillin, streptomycin, novobiocin, gentamicin, neomycin, colistin and kanamycin, or with other therapeutic agents such as probenecid.

What is claimed is:

1. A compound having the structure:

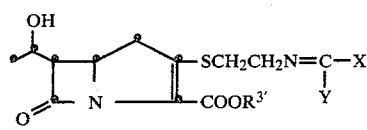

and the pharmaceutically acceptable salts thereof wherein: $R^{3'}$ is selected from the group consisting of: hydrogen, methyl, t-butyl, pivaloyloxymethyl, 2,2,2-trichloroethyl, allyl, 3-methyl-2-butenyl, benzyl, benzylhydryl, p-t-butylbenzyl, phthalidyl, phenyl, 5-indanyl, acetoxymethyl, propionyloxymethyl, methallyl, 3-butenyl, 4-pentenyl, 2-butenyl, acetoxyacetylmethyl, methoxymethyl, p-acetoxybenzyl, p-pivaloylbenzyl, p-isopropoxybenzyl, 5-indanylmethyl, benzyloxymethyl, methylthioethyl, dimethylaminoacetoxymethyl, crotonolacton-3-yl, acetamidomethyl, pivaloylthiomethyl, methylthiomethyl; X is —NR¹R² when Y is —R'—N=CRNR¹R² and X is R when Y is

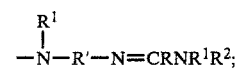

R¹ and R² at each occurance are independently selected from the group consisting of hydrogen, loweralkyl, loweralkenyl, cycloloweralkyl, loweralkylthioloweralkyl, benzyl and pyridyl; R is selected from the group consisting of hydrogen, loweralkyl, loweralkoxyloweralkyl, perfluoroloweralkyl, phenyl, pyridyl and thiazolyl; and R' is —(CH$_2$)$_n$— wherein n is an integer from 1 to 4.

2. A compound according to claim 1 wherein: R$^1$ and R$^2$ are independently selected from the group consisting of: hydrogen, loweralkyl and loweralkenyl; and R is independently selected from the group consisting of: hydrogen, loweralkyl, loweralkoxyloweralkyl, perfluoroloweralkyl, and phenyl.

3. A compound according to claim 2 wherein: R is selected from the group consisting of hydrogen, methyl, ethyl, propyl, isopropyl, methoxymethyl, trifluoromethyl, and phenyl; and R$^1$ and R$^2$ are independently selected from the group consisting of hydrogen, methyl, ethyl, propyl, isopropyl, butyl, t-butyl and allyl.

4. A compound according to claim 1 having the structure:

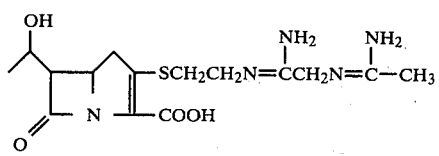

5. A compound according to claim 1 having the structure:

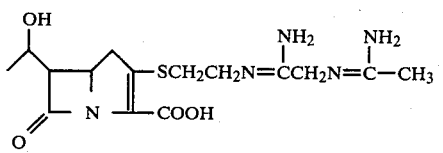

6. A compound according to claim 1 having the structure:

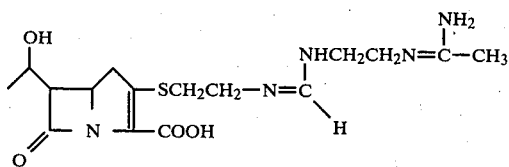

7. A compound according to claim 1 having the structure:

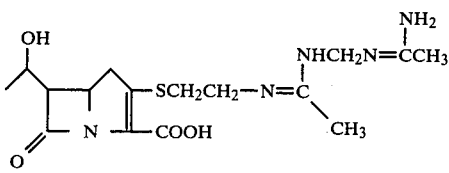

8. A compound according to claim 1 having the structure:

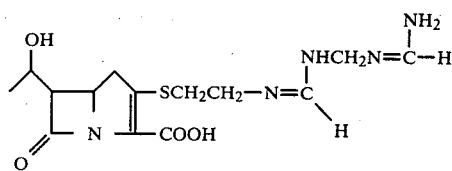

9. A compound according to claim 1 having the structure:

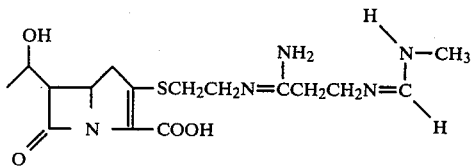

10. A compound according to claim 1 having the structure:

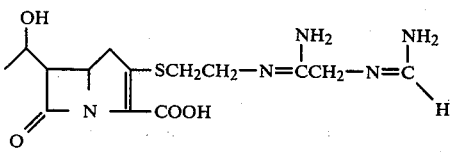

11. A compound according to claim 1 having the structure:

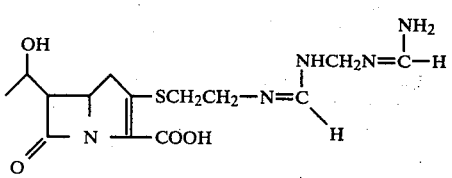

12. A compound according to claim 1 having the structure:

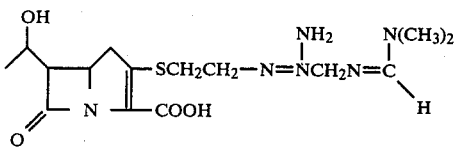

13. A compound according to claim 1 having the structure:

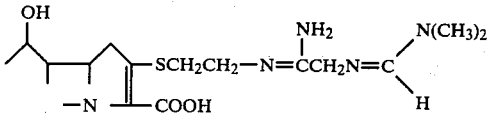

14. A compound according to claim 1 having the structure:

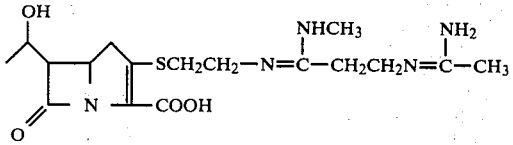

15. An antibacterial pharmaceutical composition consisting of in unitary dosage form, a therapeutically effective amount of a compound according to claim 1 and a pharmaceutical carrier therefor.

* * * * *